US007682807B2

(12) United States Patent
Zhao et al.

(10) Patent No.: US 7,682,807 B2
(45) Date of Patent: *Mar. 23, 2010

(54) ALZHEIMER'S DISEASE DIAGNOSIS BASED ON MITOGEN-ACTIVATED PROTEIN KINASE PHOSPHORYLATION

(75) Inventors: Wei-Qin Zhao, Germantown, MD (US); Daniel L. Alkon, Bethesda, MD (US)

(73) Assignee: Blanchette Rockefeller Neurosciences Institute, Morgantown, WI (US)

( * ) Notice: Subject to any disclaimer, the term of this patent is extended or adjusted under 35 U.S.C. 154(b) by 792 days.

This patent is subject to a terminal disclaimer.

(21) Appl. No.: 10/469,164

(22) PCT Filed: Feb. 27, 2002

(86) PCT No.: PCT/US02/05672

§ 371 (c)(1),
(2), (4) Date: Jul. 19, 2004

(87) PCT Pub. No.: WO02/067764

PCT Pub. Date: Sep. 6, 2002

(65) Prior Publication Data

US 2005/0059092 A1    Mar. 17, 2005

(51) Int. Cl.
*G01N 33/567* (2006.01)
*C12Q 1/00* (2006.01)
*G01N 33/00* (2006.01)

(52) U.S. Cl. .......................... 435/7.95; 435/4; 435/7.21
(58) Field of Classification Search .................. None
See application file for complete search history.

(56) References Cited

U.S. PATENT DOCUMENTS

| 5,242,932 | A | 9/1993 | Gandy et al. |
| 5,385,915 | A | 1/1995 | Buxbaum et al. |
| 6,080,582 | A | 6/2000 | Alkon et al. |
| 6,107,050 | A | 8/2000 | Alkon et al. |
| 2004/0014678 | A1 | 1/2004 | Favit et al. |

FOREIGN PATENT DOCUMENTS

| EP | 0 735 370 A | 10/1996 |
| JP | 10 090263 A | 4/1998 |
| JP | 10-090263 | 9/2007 |
| WO | WO 93 11231 A | 6/1993 |
| WO | WO 00 20867 A | 4/2000 |
| WO | 2007043998 | 4/2007 |
| WO | 2007044094 | 4/2007 |
| WO | 2007047029 | 4/2007 |

OTHER PUBLICATIONS

Growdon et al. Arch Neurol, 1999, 56(3): 281-283.*
Racchi M et al. Biochem J. 1998, 330: 1271-1275.*
Rapoport M & Ferreira A. J. Neurochem. 2000, 74: 125-133.*

Haug et al., Decreased Inositol (1,4,5)-Trisphosphate Receptor Levels in Alzheimer's Disease Cerebral Cortex: Selectivity of Changes and Possible Correlation to Pathological Severity, Neurodegeneration, vol. 5, pp. 169-176 (1996).
Young, et al., Decreased brain [3H] inositol 1,4,5-trisphosphate binding in Alzheimer's disease. Neuroscience Letters, 94 (1988), 198-202.
Kurumatani et al., Lôss of inositol 1,4,5-trisphosphate receptor sites and decreased PKC levels correlate with staging of Alzheimer's disease neurofibrillary pathology Brain Research 796 (1998) 209-221.
Blanchard, Barbara J., et al., "Hyperphosphorylation of Human TAU by Brain Kinase PK40et beyond Phosphorylation by cAMP-dependent PKA: Relation to Alzheimer's Disease." Biochem. Biophys. Res. Commun., 1994, vol. 200, No. 1, pp. 187-194.
Hyman, Bradley, T., et al., "Extracellular signal-regulated kinase (MAP Kinase) immunoreactivity in the rhesus monkey brain." Neuroscience Letters, 166 (1994) 113-116.
Gibson, Gary E., et al., "Calcium stores in cultured fibroblasts and their changes with Alzheimer's disease." Biochimica et Biophysica Acta 1316 (1996) 71-77.
Zhang, Liang, et al., "Oxidative stress differentially modulates phosphorylation of ERK, p38 and CREB induced by NGF or EGF in PC12 cells." Neurobiology of Aging 20 (1999) 271-278.
Laporte, Johanne D., et al., "Role of ERK MAP kinases in responses of cultured human airway smooth muscles cells to IL-1B." Am. J. Physiol. Lung Cell Mol. Physiol., 1999, vol. 277, pp. 943-951.
Bernier, Sylvie G., et al., "Bradykinin-regulated Interactions of the Mitogen-activated Protein Kinase Pathway with the Endothelial Nitric-oxide Synthase." J. Biol. Chem., 2000, vol. 275, pp. 30707-30715.
European Search Report for EP 02 72 3236 dated Mar. 24, 2004.
Etcheberrigaray, Rene, et al., "Molecular Mechanisms of Memory and the Pathophysiology of Alzheimer's Disease", Anals New York Academy of Sciences, vol. 474, Issue 1 245-255 (1994).
Pascale, Alesia, et al., "Enhanced BK-induced calcium responsiveness in PC12 cells expressing the C100 fragment of the amyloid precursor protien", Molecular Brain Research 72 (1999) 205-213.
Zhao, Wei-Qin, et al., "Map kinase signaling cascade dysfunction specific to Alzheimer's disease in fibroblasts," Neurology of Disease. United States Oct. 2002, vol. 11, No. 1, Oct. 2002, pp. 166-183, XP002272831, ISSN: 0969-9961.
Baker et al. "System Manifestation of Alzheimer's Disease," Age, vol. 11, 60-65, 1988.
Huynh et al. "Reduced Protein Kinase C Immunoreactivity and Altered Protein Phosphorylation in Alzheimer's Disease Fibroblasts," Arch Neurol, vol. 46, Nov. 1989.

(Continued)

*Primary Examiner*—John D. Ulm
*Assistant Examiner*—Stacey MacFarlane
(74) *Attorney, Agent, or Firm*—Milbank, Tweed, Hadley & McCloy, LLP

(57) ABSTRACT

A method of diagnosing Alzheimer's disease in a patient comprises determining whether the phosphorylation level of an indicator protein in cells of the patient after stimulus with an activator compound is abnormally elevated as compared to a basal phosphorylation level, the indicator protein being e.g. Erk1/2 and the activator compound being e.g. bradykinin.

62 Claims, 8 Drawing Sheets

OTHER PUBLICATIONS

Masliah et al. "Protein Kinase C Alteration is An Early Biochemical Marker in Alzheimer's Disease," The Journal of Neuroscience, Sep. 1991, 11(9):2759-2767.
Caporaso et al. "Protein phosphorylation regulates secretion of Alzheimer B/A4 amyloid precursor protein," Proc. Natl. Acad. Sci. USA, vol. 89, pp. 3055-3059, Apr. 1992.
Gillespie et al. "Secretory Processing of the Alzheimer Amyloid B/A4 Protein Precursor is Increased by Protein Phosphorylation," Biochemical and Biophysical Communications, vol. 187, No. 3, 1992.
Etcheberrigary et al. "Potassium channel dysfunction in fibroblasts identifies patients with Alzheimer disease," Proc. Natl. Acad. Sci. USA, vol. 90, pp. 8209-2813, Sep. 1993.
Govoni et al, "Cytosol protein kinase C downregulation in fibroblasts from Alzheimer's disease patients," Neurology, 43 2581, Dec. 1993.
Jin et al. "Changes in Protein Kinases in Brain Aging and Alzheimer's Disease," Drugs & Aging, 6(2):130-149, 1995.
Scott, "Extraneuronal Manifestations of Alzheimer's Disease, "JAGS 41:268-276, 1993.
Huang, et al. "Inositol phosphates and intracellular calcium after bradykinin stilumation in fibroblasts from young, normal aged and Alzheimer donors," Neurobiology of Aging, US 1991, Sep.-Oct. vol. 12, No. 5, Sep. 1991, pp. 469-473, XP009027346, ISSN: 0197-4580.
Tanzi et al. "The Gene Defects Responsible for Familial Alzheimer's Disease," Neurology of Disease, 3, 159-168 (1996).
Hirashima et al. "Calcium Responses in Human Fibroblasts: A Diagnostic Molecular Profile for Alzheimer's Disease,." Neurology of Aging, vol. 17, No. 4, pp. 549-555, 1996.
Burke et al. "Update on Alzheimer's disease. Promising advances in detection and treatment," Postgraduate Medicine, vol. 106, No. 5, Oct. 1999.
Zhao, W.Q., et al. "Dysfunction of MAP Kinase signaling in Alzheimer's disease," Society of Neuroscience, Abstracts, vol. 27, No. 1, 2001, p. 924, 31st Annual Meeting of the Society of Neuroscience, San Diego, CA, USA, Nov. 10-15, 2001, ISSN: 0190-5295.
Huang et al. "Increased Inositol 1, 4, 5-Trisphosphate Accumulation Correlates Withan Up-Regulation of Bradykinin Receptors in Alzheimer's Disease," Journal of Neurochemistry, New York, NY, US, vol. 64, No. 2, Feb. 1, 1995, pp. 761-766 XP002052582, ISSN: 0022-3042.
El-Dahr, S.S., et al. "Bradykinin stimulates the ERKfwdanwElk-1fwdanwFos/AP-1 pathway in nesagial cells," American Journal of Pysiology, vol. 275, No. 3, Part w, Sep. 1998 (1998-09) pp. F343-F352, ISSN: 0002-9513.
Sato, N, et al. "Elevated amyloid beta protein (1-40) level induces CREB phosphorylation at serine-133 via p44/42 MAP kinase (Erk1/2)-dependent pathway in rat pheochromocytoma PC12 cells," Biochemical and Biophysical Research Communications, US Mar. 27, 1997, vol. 232, No. 3, pp. 637-642, ISSN: 0006-291X.
Bassa BV, et al. VS (1999) Am J Physiol 277, F328-2337.
Berridge et al. (1984) Biochem J 220, 345-360.
Bondy et al. "The PHA-Induced Calcium Signal in Lymphocytes is Altered After Blockade of K+-Channels in Alzheimer's Disease," J.pschiat. Res., vol. 30, No. 3, pp. 217-227, 1996.
Gibson et al. (1996) Biochim, Biophys Acta 1316, 71-77.
Ito et al. "Internal Ca2+mobilization is altered in fibroblasts from patients with Alzheimer disease." Proc Natl Acad Sci USA 91, 534-538.
Biernat et al. (1993) Neuro 11, 153-163.
Ekinci and Shea (1999) Cell Mol. Neurobiol. 19, 249-260.
Etcheberrigaray et al. Molecular mechanisms of memory and the pathophysiology of Alzheimer's disease,: Ann NY Acad Sci 747:345-55.
Etcheberrigary et al. (1998) Neurobiol. Disease. 5, 37-45.
Pascale et al. "Enhanced BK-induced calcium responsiveness in PC12 cells expressing the C100 fragment of the amyloid precursor protein," Brain Res Mol Brain Res 72:205-2.
Grant et al. (1999) Brain Res Mol Brain Res. 72, 115-20.
Greenberg et al. "Secreted beta-amyloid precursor protein stimulates mitogen-activated protein kinase and enhances tau phosphorylation," Proc Natl Acad Sci USA 91, 7104-7108 (1994).
Lu et al. (1993) J. Neurosci. Res. 35, 439-444.
McDonald et al. (1998) J Neurosci 18, 4451-4460.
Reynolds et al. (2000) J. Neurochem. 74, 1587-1595.
U.S. Appl. No. 11/246, 524, filed Oct. 11, 2005, Zhao et al.
U.S. Appl. No. 12/083,056, filed Sep. 25, 2006, Zhao et al.
Favit, Antonella, et al., "Alzheimer's-specific effects of soluble B-amyloid on protein Kinase C-a and -y degradation in human fibrolasts", Proc. Natl. Acad. Sci. USA, vol. 95, pp. 5562-5567, May 1998 .

* cited by examiner

FIGURE 5A
FIGURE 5B1 
FIGURE 5B2 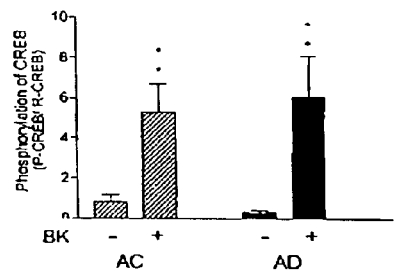
FIGURE 5C1 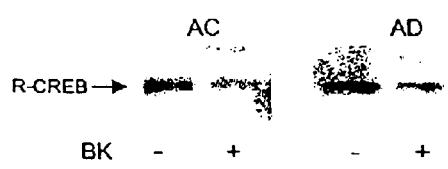
FIGURE 5C2 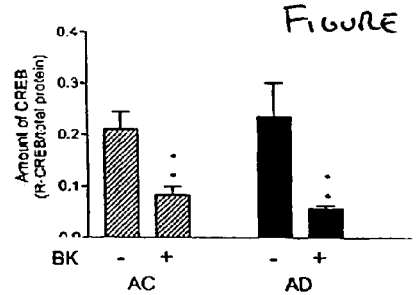
FIGURE 5

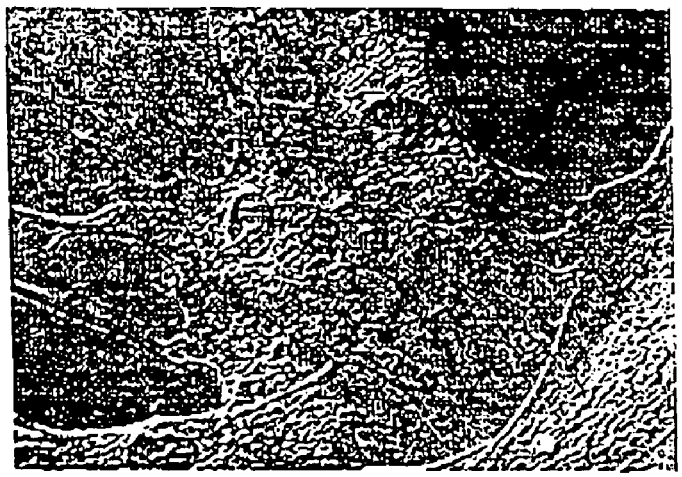
FiGURE 7A
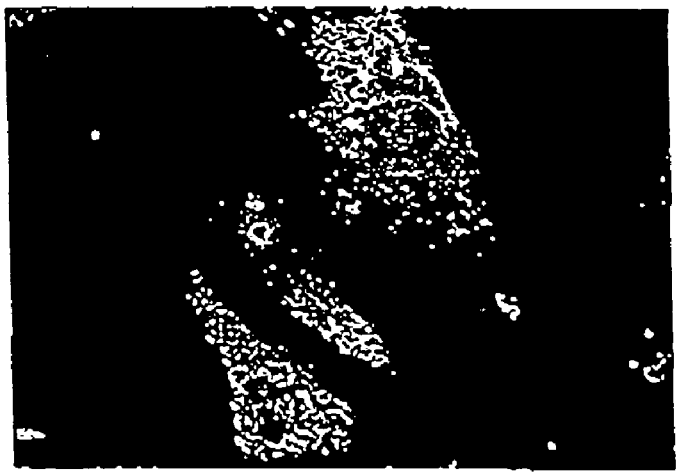
FiGURE 7 B
FIGURE 7

ALZHEIMER'S DISEASE DIAGNOSIS BASED ON MITOGEN-ACTIVATED PROTEIN KINASE PHOSPHORYLATION

BACKGROUND OF THE INVENTION

The invention provides a diagnostic and screening test for Alzheimer's disease ("AD"). An example of the test involves detecting abnormally enhanced phosphorylation of extracellular signal-regulated kinase type 1 or 2 ("Erk1/2") in skin fibroblasts from AD patients after stimulating the cells with agonist such as bradykinin or other agents that stimulate the inositol 1,4,5-trisphosphate (IP3) receptor, in comparison to cells from age-matched controls. Enhanced phosphorylation may be measured by Western blot using antibodies specific for the phosphorylated protein or other similar approaches.

Accumulating evidence indicates that the early pathogenesis of Alzheimer's disease (AD) involves perturbation of intracellular calcium homeostasis and increased levels of oxidative stress that contribute to excitatory toxicity and neuronal death in the AD brain (Putney, 2000; Yoo et al., 2000; Sheehan et al., 1997). Studies have reported enhanced elevation of intracellular $Ca^{2+}$ levels in AD brains as well as in peripheral cells in response to activation of bradykinin receptors and inactivation of a $K^+$ channel (Ito et al., 1994; Etcheberrigaray et al., 1994; Hirashima, et al., 1996; Gibson et al., 1996; Etcheberrigaray et al., 1998). Critical proteins such as amyloid precursor protein (APP), presenilin 1 and presenilin 2, mutations of which are associated with the pathogenesis of AD, have been reported to induce dysregulation of both the IP3 receptor (IP3R) and the ryanodine receptor-(RYR-) mediated intracellular $Ca^{2+}$ homeostasis (Yoo et al., 2000; Leissring et al., 1999; 2000; Mattson et al., 2000; Barrow et al., 2000). The alteration in cytosolic $Ca^{2+}$ concentration is thought to contribute to the pathophysioloy of AD, including increased production of the neurotoxic 42 amino acid β-amyloid peptide (APβ) involved in plaque formation, hyperphosphorylation of tau protein involved in formation of neurfibrillay tangles, and enhanced general vulnerability of neurons to cell death.

Bradykinin (BK) is a potent vasoactive nonapeptide that is generated in the course of various inflammatory conditions. BK binds to and activates specific cell membrane BK receptor(s), thereby triggering a cascade of intracellular events leading to the phosphorylation of proteins known as "mitogen activated protein kinase" (MAPK; see below). Phosphorylation of proteins, the addition of a phosphate group to a Ser, Thr or Tyr residue, is mediated by a large number of enzymes known collectively as protein kinases. Phosphorylation normally modifies the function of, and usually activates, a protein. Homeostasis requires that phosphorylation be a transient process, which is reversed by phosphatase enzymes that dephosphorylate the substrate. Any aberration in phosphorylation or dephosphorylation disrupts biochemical pathways and multiple cellular functions. Such disruptions may be the basis for certain brain diseases.

Increased intracellular $Ca^{2+}$ levels in response to BK is mediated at least by the "type 2" BK receptor (BKb2R), a G-protein-coupled receptor. Stimulation of BKb2R by BK activates phospholipase C (PLC) resulting in production of diacylglycerol (DAG) and inositol 1,4,5-trisphosphate (IP3), second messengers involved in regulation of intracellular $Ca^{2+}$ levels and activation of protein kinase C (PKC). The PLC/phospholipid/PKC pathway also interact with the Ras signaling pathway that activates the MAPK pathway. MAPK (or MAP kinase) refers to an enzyme family termed "mitogen activated protein kinase," an important member of which is the "extracellular signal-regulated kinase" type 1 or 2 ("Erk1/2") (Berridge, 1984; Bassa et al., 1999). Erk1/2 receive signals from multiple signal transductional pathways and is part of a pathway that leads to cell proliferation and differentiation by regulation of gene expression through a number of transcriptional factors including cyclic adenosine monophosphate (cAMP)-responsive element binding protein (CREB).

Erk1/2 phosphorylates tau protein at multiple Ser/Thr sites including Ser262 and Ser356 (Reynolds et al., 2000), which are in microtubule-binding regions of tau. Phosphorylation of Ser262 markedly compromises the ability of tau to assemble and stabilize microtubules (Biemat et al., 1993; Lu et al., 1993). Increased oxidative stress, aberrant expression of amyloid precursor protein (APP), and exposure to APβ cause activation of MAPK (McDonald et al., 1998; Ekinci and Shea, 1999; Grant et al., 1999) and enhanced tau phosphorylation (Greenberg et al., 1994).

Young L T et al., *Neurosci Lett,* 1988, 94:198-202 studied IP3 receptor binding sites in autopsied brains from 10 subjects with AD and 10 age-matched controls. In the parietal cortex and hippocampus, there was a 50-70% loss of [$^3$H]-IP3 binding whereas no significant changes were observed in frontal, occipital and temporal cortices, caudate or amygdala. Scatchard analysis confirmed a reduction in receptor density rather than a change in affinity. Also, many neurotransmitters, hormones and growth factors act at membrane receptors to stimulate the phosphodiesterase hydrolysis of phosphatidylinositol 4,5-bisphosphate (PIP2) generating the comessengers IP3 and diacylglycerol (DAG). DAG stimulates PKC while IP3 was initially postulated to activate specific receptors leading to release of intracellular calcium, probably from the endoplasmic reticulum.

Though earlier reports had detected $^{32}$P-IP3 binding to liver and adrenal microsomes and to permeabilized neutrophils and liver cells, Solomon Snyder's group was the first to localize, isolate, analyze and later clone, IP3 receptors. Worley P F et al., Nature 1987;325:159-161, demonstrated high affinity, selective binding sites for $^3$H- and $^{32}$P-labelled IP3 in the brain at levels 100-300 times higher than those observed in peripheral tissues. These receptors were considered physiologically relevant because the potencies of various myo-inositol analogues at the IP3 binding site corresponded to their potencies in releasing calcium from microsomes. Brain autoradiograms demonstrated discrete, heterogeneous localization of IP3 receptors. In 1988, this group (Supattapone S et al., *J Biol Chem,* 1988, 263:1530-1534, reported the solubilization, purification to homogeneity, and characterization of an IP3 receptor from rat cerebellum. The purified receptor was a globular protein that migrated in electrophoresis as one protein band with an Mr of 260 kDa. In a review, Snyder et al. (*Cell Calcium,* 1989, 10:337-342) noted that immunohistochemical studies with antisera to the purified receptor protein localized the receptor to a subdivision of the rough endoplasmic reticulum occurring in synaptic areas and in close association with the nuclear membrane. The IP3 receptor protein was selectively phosphorylated by cAMP-dependent protein kinase. This phosphorylation decreased 10-fold the potency of IP3 in releasing calcium from brain membranes. Ferris C D et al., *Proc Natl Acad Sci USA,* 1991 88:2232-2235 later studied phosphorylation of IP3 receptors with purified receptor protein reconstituted in liposomes (to remove detergent that can inhibit protein kinases). The IP3 receptor was stoichiometrically phosphorylated by protein kinase C (PKC) and CaM kinase II as well as by protein kinase A (PKA). IP3 receptors are regulated by phosphorylation catalyzed by the three enzymes which was additive and involved different peptide sequences. Phosphorylation by (1) PKC which was stimulated by $Ca^{2+}$ and DAG, and (2) by CaM kinase II which required $Ca^{2+}$, provided a means whereby $Ca^{2+}$ and DAG, formed during inositol phospholipid turnover, regulate IP3 receptors. Chadwick C C et al., *Proc Natl Acad Sci USA,* 1990 87:2132-2136, described the isolation from smooth muscle of an IP3 receptor that was an oligomer of a single polypeptide with a Mr of 224 kDa. Furuichi T, et al., *FEBS Lett,* 1990 267:85-88 examined distribution of IP3 receptor mRNA in mouse tissues. The concentration of was greatest in cerebellar tissue. Moderate amounts of IP3 receptor mRNA were present in other brain tissue: thymus, heart, lung, liver, spleen, kidney, and uterus. Small amounts of IP3 receptor mRNA were observed in skeletal muscle and testicular tissue. Based on in situ hybridization, a considerable amount of IP3 receptor mRNA was located in smooth muscle cells, such as those of the arteries, bronchioles, oviduct and uterus. Ferris C D et al., *J Biol Chem,* 1992, 267:7036-7041, demonstrated serine autophosphorylation of the purified and reconstituted IP3 receptor and found serine protein kinase activity of the IP3 receptor toward a specific peptide substrate. The investigators concluded that the IP3 receptor protein and the phosphorylating activity reside in the same molecule. Ross C A et al. (*Proc Natl Acad Sci USA,* 1992, 89:4265-4269), cloned three IP3R cDNAs, designated IP3R-II, -III, and -IV, from a mouse placenta cDNA library. All three displayed strong homology in membrane-spanning domains M7 and M8 to the originally cloned cerebellar IP3R-I, with divergences predominantly in cytoplasmic domains. Levels of mRNA for the three additional IP3Rs in general were substantially lower than for IP3R-I, except for the gastrointestinal tract where levels were comparable. Cerebellar Purkinje cells expressed at least two and possibly three distinct IP3Rs, suggesting heterogeneity of IP3 action within a single cell. Sharp A H, *Neuroscience,* 1993, 53:927-42, examined in detail the distribution of IP3 receptors in the rat brain and spinal cord using immunohistochemical methods. IP3 receptors are present in neuronal cells, fibers and terminals in a wide distribution of areas throughout the CNS, including the olfactory bulb, thalamic nuclei and dorsal horn of the spinal cord, in circumventricular organs and neuroendocrine structures such as the area postrema, choroid plexus, subcommisural organ, pineal gland and pituitary. Ca2+ release mediated by the phosphoinositide second messenger system is important in control of diverse physiological processes. Studies of IP3 receptors in lymphocytes (T cells) by Snyder's group localized these receptors to the plasma membrane. Capping of the T cell receptor-CD3 complex, which is associated with signal transduction, was accompanied by capping of IP3 receptors. The IP3 receptor on T cells appears to be responsible for the entry of $Ca^{2+}$ that initiates proliferative responses (Khan, A A et al., *Science,* 1992, 257:815-818)

Further with regard to IP3, Wilcox R A et al., *Trends Pharmacol Sci,* 1998, 19:467-475, noted that receptor-mediated activation of PLC to generate IP3 is a ubiquitous signalling pathway in mammalian systems. A family of three IP3 receptor subtype monomers form functional tetramers, which act as IP3 effectors, providing a ligand-gated channel that allows $Ca^{2+}$ ions to move between cellular compartments. As IP3 receptors are located principally, although not exclusively, in the endoplasmic reticular membrane, IP3 is considered to be a second messenger that mobilizes $Ca^{2+}$ from intracellular stores contributing to a variety of physiological and pathophysiological phenomena. Patel S et al., *Cell Calcium,* 1999, 25:247-264, reviewed the molecular properties of IP3 receptors. Several $Ca^{2+}$-binding sites and a $Ca^{2+}$-calmodulin-binding domain were mapped within the type I IP3 receptor, and studies on purified cerebellar IP3 receptors suggested a second $Ca^{2+}$-independent calmodulin-binding domain. Overexpression of IP3 receptors provided further clues to the regulation of individual IP3 receptor isoforms present within cells, and the role that they play in the generation of IP3-dependent $Ca^{2+}$ signals. IP3 receptors may be involved in cellular processes such as proliferation and apoptosis. Abdel-Latif AA. Exp Biol Med (Maywood) 2001 March;226(3):153-63 reviewed evidence, both from nonvascular and vascular smooth muscle, for cross talk between the cyclic nucleotides, cAMP and cGMP via their respective protein kinases, and the $Ca^{2+}$-dependent- and $Ca^{2+}$-independent-signaling pathways involved in agonist-induced contraction. These included the IP3-$Ca^{2+}$-CaM-myosin light chain kinase (MLCK) pathway and the $Ca^{2+}$-independent pathways, including PKC, MAP kinase, and Rho-kinase. Mikoshiba K et al., Sci STKE 2000 Sep. 26;2000(51):P, described the regulated release of calcium from intracellular stores by the IP3 receptor and the relationship of this release mechanism to calcium influx from the extracellular milieu through store-operated calcium channels. They disclosed a model of functional and physical coupling of intracellular and plasma membrane calcium channels.

Although AD is well known for its severe brain damage and memory loss, pathological changes are manifest elsewhere in the body and can be detected at the cellular level. Skin fibroblasts lying in the deep layer of skin reveal characteristic cellular and molecular abnormalities of AD damage. Skin fibroblasts are readily obtained and cultured for diagnostic purposes (U.S. Pat. No. 6,107,050, "Diagnostic Test for Alzheimer's Disease," issued Aug. 22, 2000, which is incorporated herein by reference). However, there is a need for simpler, more economical, accurate and reliable methods for diagnosis of Alzheimer's disease.

It is known e.g. from U.S. Pat. No. 6,107,050, Alkon et al., that differential effects of an activator of intracellular Ca2+ release can be measured. Both healthy and Alzheimer's cell types exhibit a release of calcium from storage, but Alzheimer's cells exhibit a much greater release. Known methods for measuring the release of Ca2+(i) include fluorescent indicators, absorbance indicators or a Ca2+"patch clamp" electrode, and others, and such methods may be used for diagnostic purposes. However, there is a tremendous need for more effective techniques for measuring the differential effects of IP3R activators, for diagnostic, research, and clinical purposes.

SUMMARY OF THE INVENTION

The invention provides a method of diagnosing Alzheimer's disease in a patient comprising detecting the presence or absence of an abnormally elevated level of a phosphorylated indicator protein in cells of the patient after activating the cells with a compound that stimulates phosphorylation of the indicator protein, the presence of such an elevated level indicating a positive diagnosis for Alzheimer's disease.

The diagnostic method comprises measuring a phosphorylation level of an indicator protein in cells of the patient at a predetermined time after stimulating the cells with an activator compound, and determining comparing the stimulis abnormally elevated as compared to a basal phosphorylation level without stimulus.

The invention provides a method of diagnosing Alzheimer's disease in a subject, said method comprising: (a) measuring a basal level of phosphorylation of an indicator protein in cells from the subject; (b) contacting cells from the subject with an activator compound, the activator compound and indicator protein being selected such that the activator elicits a differential response of activated phosphorylation of the indicator protein in cells of the subject as compared to an activated phosphorylation response in cells from a non-Alzheimer's control subject at a predetermined time after the contacting is initiated; (c) measuring an activated phosphorylation level of the indicator protein in said subject cells at the predetermined time after contacting is initiated; and (d) calculating a ratio of the activated phosphorylation level determined in step (c) to the basal phosphorylation level of step (a); and (e) comparing the calculated ratio of step (d) to previously determined activated phosphorylation ratios measured from known Alzheimer's disease cells and from known non-Alzheimer's disease cells at said predetermined time; wherein if the calculated ratio is not statistically different from the previously determined ratios for said known Alzheimer's disease cells, the diagnosis is positive, and/or if the calculated ratio is not statistically different from the previously determined ratios for said known non-Alzheimer's disease cells, the diagnosis is negative.

The invention further provides a method of diagnosing Alzheimer's disease in a subject comprising: in cells of the subject, measuring a background phosphorylation level of an indicator calcium signalling pathway protein whose phosphorylation is associated with IP-3R-sensitive $Ca^{2+}$ elevation in the cells; stimulating cells of the subject by contact with an IP3R agonist that elicits a differential response in the phosphorylation level of the indicator protein in cells of Alzheimer's subjects as compared to the level in a non-Alzheimer's control cell; thereafter, measuring a response phosphorylation level of the indicator protein in the contacted cells, and determining whether the response phosphorylation level of the indicator protein as compared to the background level matches the response level known for a cell from an Alzheimer's subjects or from a healthy control cell.

The methods may comprise first measuring the background phosphorylation level of the indicator protein in a culture of cells, then adding the IP3R agonist to the culture, and measuring the response phosphorylation level. Or the method may comprise measuring the background level in a first aliquot of cells, stimulating a similar aliquot of the cells, and measuring the response level in the aliquot.

The activator compound may be an IP3-R agonist selected from the group consisting of bradykinin, bombesin, cholecystokinin, thrombin, prostaglandin $F_{2\alpha}$ and vasopressin.

The cells may be selected from the group consisting of fibroblasts, buccal mucosal cells, neurons, and blood cells.

According to the invention, a method of diagnosing Alzheimer's disease in a subject comprises (a) obtaining cells from said subject; (b) measuring the basal level of phosphorylation of an indicator protein in said cells; (c) contacting said cells with an activator of phosphorylation of the indicator protein; (d) measuring the phosphorylation level of the indicator protein in said cells at a predetermined time after initiation of the contacting; and (e) calculating a first ratio of the level measured in step (d) to the level measured in step (b) and comparing said first ratio to a previously determined second ratio of said levels obtained at said predetermined time from known Alzheimer's disease cells and a third ratio of said levels obtained at said predetermined time from known non-Alzheimer's disease cells; wherein (i) if the first ratio of step (e) is statistically not different from the previously determined second ratio, the diagnosis is positive, and (ii) if the first ratio of step (e) is not statistically different from the previously determined third ratio, the diagnosis is negative. The predetermined time of step (d) may be a time when the difference between the second ratio and the third ratio of step (e) is greatest.

In the inventive methods, the measuring may comprise an immunoassay of disrupted cells, and the subject's cells may be contacted with an antibody specific for the phosphorylated indicator protein, permitting the antibody to bind to the indicator protein, and detecting the antibody bound to the indicator protein. The immunoassay may be a radioimmunoassay, a Western blot assay, an immunofluorescence assay, an enzyme immunoassay, an immunoprecipitation assay, a chemiluminescence assay, an immunohistochemical assay, a dot blot assay, or a slot blot assay.

A further inventive method of diagnosing Alzheimer's disease in a subject comprises:

(a) incubating cells from said subject with a compound in a diluent, wherein the compound stimulates calcium signaling pathway-mediated phosphorylation of an indicator protein, thereby producing stimulated cells;

(b) before, at the same time or after step (a) incubating cells of the same type from the subject with a control compound or with said diluent, thereby producing unstimulated control cells;

(c) comparing a level of the phosphorylated indicator protein in the stimulated cells to a level of phosphorylated indicator protein in the unstimulated control cells, wherein an increase in the level of the phosphorylated indicator protein in stimulated cells as compared to the unstimulated cells indicates the presence of Alzheimer's disease.

The comparing step (c) may include the following steps: (i) contacting a protein sample from said stimulated and/or said unstimulated cells with an antibody which recognizes the phosphorylated indicator protein; and (ii) detecting the binding of said antibody to said indicator protein.

The method may further comprise contacting a protein sample from said stimulated and/or said unstimulated cells with an antibody which recognizes an unphosphorylated form of said indicator protein, and detecting the binding of said antibody and unphosphorylated indicator protein, and normalizing the level of protein. The comparing step may further include the step of obtaining a protein sample from said stimulated and said unstimulated cells.

A method of diagnosing the presence of Alzheimer's disease in a subject may comprise the steps of: a) stimulating cells from said subject with an activator compound that increases phosphorylation of an indicator protein, and b) comparing the level of unphosphorylated indicator protein and phosphorylated indicator protein in stimulated cells to the level of unphosphorylated indicator protein and phosphorylated indicator protein in unstimulated cells of the same type from said subject, wherein an increase in the relative level of phosphorylated indicator protein in stimulated cells as compared to unstimulated cells indicates the presence of Alzheimer's disease.

The invention provides a method of diagnosing Alzheimer's disease in a subject, comprising: contacting cells from the subject with an agent that triggers intracellular calcium release via the inositol 1,4,5-trisphosphate (IP3) receptor, measuring the amount of phosphorylation of a MAPK protein in the subject's cells at one or more time points after the contacting step, and comparing the amount of phosphorylation of the MAPK protein in the subject's cells at the one or more time points with the amount of phosphorylation in cells from a non-Alzheimer's control subject at the same time points after contacting the control cells with the agent, wherein increased phosphorylation of the MAPK protein in the subject's cells compared to the control cells is diagnostic of Alzheimer's disease.

In the methods of the invention, the agent may be bradykinin or a bradykinin receptor agonist, or bombesin, and may be an agonist which induces IP3-mediated $Ca^{2+}$ release.

The amount of phosphorylation may be measured at a single time point after the contacting step. According to the invention, the measuring may comprise measuring the amount of phosphorylation in a first aliquot of the subject's cells at a first time point after the contacting step, and measuring the amount of phosphorylation in a second aliquot of the subject's cells at a second time point after the contacting step. The time points may be about 0.5 minutes or shorter, 1 minute, 2 minutes, 2.5 minutes, 5 minutes, 10 minutes, 20 minutes, 30 minutes, 45 minutes, or 1 hour, or longer for some combinations of cell types, activators, and indicator proteins.

The cells are typically from peripheral tissue, such as skin fibroblasts.

The measuring step in the inventive methods optionally comprises detecting phosphorylation in a lysate of the subject's cells, in vitro, and may comprise gel electrophoresis, Western blotting, using an anti-phospho-MAPK antibody and/or an anti-regular MAPK protein antibody.

The increased phosphorylation may be an elevation in the amount of phosphorylated protein at a single time point or an increase in duration of the phosphorylated protein The methods are effective in diagnosis where the subject lacks clinical manifestations of Alzheimer's disease.

According to the invention, the methods may further comprise contacting the subject's cells with one or more inhibitors selected from the group consisting of an inhibitor of protein kinase C activity, an inhibitor of PI-3 kinase activity, an inhibitor of C-src protein tyrosine kinase activity, an inhibitor of the IP-3 receptor and an inhibitor of a protein phosphatase. Also, by way of characterizing a particularly discriminating embodiment of the invention, the methods may be characterized as having the increased phosphorylation inhibited by contacting the subject's cells with an inhibitor selected from the group consisting of an inhibitor of protein kinase C activity, C-src protein tyrosine kinase activity, PI-3 kinase activity, and the IP-3 receptor. In such methods said inhibitor can be selected from the group consisting of BiSM-1, PP1, and 2-aminoethoxydiphenyl borate.

The invention further provides a method for screening compounds to identify a compound useful for treatment or prevention of Alzheimer's disease comprising:

contacting test cells from an AD subject with a compound being screened, before, during, or after the contacting step, stimulating the test cells with an agent that triggers intracellular calcium release via the inositol 1,4,5-trisphosphate (IP3) receptor, measuring the amount of phosphorylation of a MAPK protein in the test cells at one or more time points after stimulating the test cells, comparing the amount of phosphorylation of the MAPK protein in the test cells at the one or more time points with the amount of phosphorylation at the same one or more time points in control cells from an AD subject that are not contacted with the compound.

The methods may further comprise accepting a compound that inhibits or prevents the increased phosphorylation as a lead compound, and rejecting a compound that does not inhibit or prevent the increased phosphorylation. As in all the methods of the invention, the agent may be bradykinin or a bradykinin receptor agonist and the the MAPK protein may be Erk1/2. The methods may comprise measuring the amount of phosphorylation at a single time point after the contacting step.

A further embodiment provides a method of screening compounds for usefulness as activator compounds in a stimulus-response assay, comprising measuring the effect of the compound on phosphorylation of an indicator protein in AD cells and control cells and selecting a compound that increases phosphorylation of the indicator protein in amount and/or duration in AD cells as compared to control cells.

Another embodiment of the invention is a diagnostic test kit for Alzheimer's disease comprising anti-phospho-MAPK protein antibody and bradykinin.

An embodiment provides a method for selecting medication for an Alzheimer's patient comprising selecting a possible therapeutic compound, administering the possible therapeutic compound to the patient, and thereafter, detecting the presence or absence of an abnormally elevated level of a phosphorylated indicator protein in cells of the patient after activating the cells with a compound that stimulates phosphorylation of the indicator protein, the presence of such an elevated level indicating that the possible therapeutic compound is not effective for the patient, and the absence of such a level indicating that the possible therapeutic compound is therapeutic for the patient. The method may further comprise treating or preventing Alzheimer's disease in the subject by administering to the subject the compound shown to be therapeutic for the patient.

The invention provides a method of treating or preventing Alzheimer's disease in a subject comprising administering an effective amount of a medicament that (a) inhibits or prevents abnormally elevated phosphorylation of a MAPK protein in cells of the subject as compared to control cells; and/or (b) inhibits events caused by abnormally elevated phosphorylation of said MAPK protein.

The medicament may inhibit Erk1/2 phosphorylation, and may be an inhibitor of protein kinase C activity. src protein tyrosine kinase activity, or the IP-3 receptor. The inhibitor may be selected from the group consisting of BiSM-1, PP 1, and 2ABP.

In particular, the invention provides a method of diagnosing Alzheimer's disease in a subject, comprising:

(a) contacting skin fibroblast cells from the subject and from a non-Alzheimer's control subject with an effective, phosphorylation-stimulating concentration of bradykinin, (b) measuring the amount of phosphorylated Erk1/2 in the subject's cells at one or more time points selected from the group consisting of 2 minutes, 5 minutes, 10 minutes, 20 minutes, and 30 minutes, by Western blotting using an antibody specific for phospho-Erk1/2;

(c) measuring the amount of phosphorylated Erk1/2 in cells from a non-Alzheimer'S control subject at the same time point or points as in (b) by Western blotting using an antibody specific for phospho-Erk1/2, wherein the amount of phosphorylated Erk1/3 in steps (b) and (c) is normalized to the amount of protein present in said cells;

(d) comparing the amount of phosphorylated Erk1/2 in the subject's cells with the amount of phosphorylated Erk1/2 in the control cells at said time points, wherein an increased amount of phosphorylated Erk1/2 in the subject's cells compared to the control cells at one of more of said time points is diagnostic of Alzheimer's disease.

The method may further comprise contacting the subject's cells with one or more inhibitors selected from the group consisting of the inhibitor of protein kinase C activity, BiSM-1, the inhibitor of C-src protein tyrosine kinase activity, PP1; and the inhibitor of the IP-3 receptor, 2-aminoethoxydiphenyl borate, wherein the bradykinin-induced increase in the amount of phosphorylated Erk1/2 in the subject's cells compared to the control cells is reduced by said inhibitor.

A further embodiment of the invention provides a method for screening compounds to identify a compound useful for treatment or prevention of Alzheimer's disease comprising:
(a) contacting test skin fibroblasts from an AD subject with a compound being screened;
(b) contacting control skin fibroblasts from said subject with a control agent for said compound or incubating said control fibroblasts in the absence or either said compound or said control agent;
(c) before, during, or after step (a) and (b) stimulating the test and the control fibroblasts with an effective, phosphorylation-stimulating concentration of bradykinin,
(d) measuring the amount of phosphorylated Erk1/2 in the test and in the control fibroblasts at one or more time points selected from the group consisting of 2 minutes, 5 minutes, 10 minutes, 20 minutes, and 30 minutes, by Western blotting using an antibody specific for phospho-Erk1/2, wherein the amount of phosphorylated Erk1/3 is normalized to the amount of protein present in said test and control fibroblasts;
(e) comparing the amount of phosphorylated Erk1/2 in the test fibroblasts with the amount of phosphorylated Erk1/2 in the control fibroblasts, to determine whether the compound inhibits or prevents bradykinin-induced increase in phosphorylation of Erk1/2 in the test cells compared to the control cells, wherein a compound that inhibits or prevents the increased phosphorylation is identified as useful for the treatment of prevention of Alzheimer's disease.

A method of the invention is a method of reducing proteolysis of amyloid precursor protein, secretion of amyloid protein β, and/or phosphorylation of tau protein in a human cell, the cell having increased IP3 receptor mediated phosphorylation of MAPK protein compared to a control human cell, comprising contacting the cell with an inhibitor of phosphorylation of MAPK effective to reduce phosphorylation to the level in the control cell The elements of the invention recited herein may be combined or eliminated among the particular embodiments described, as would be apparent to a person of ordinary skill.

BRIEF DESCRIPTION OF THE DRAWINGS

FIGS. 1A1, 1A2 and 1B. Time course of the BK-stimulated activation of Erk1/2. AD cells and cells from age-matched normal controls ("AC") were treated with 10 nM BK for different times and the reactions were terminated as described in the Examples. To the control for each cell line was added the same volume of PBS. The top images were representative Western blots for activated Erk1/2 (P-Erk1/2) from AD and AC cells. The mean density of each sample was normalized to the total amount of protein, which was determined using a anti-"regular MAP kinase" antibody (R-Erk1/2). Statistical significance of values from 11 independent cell lines was evaluated by an unpaired Student's t-test. Results are summarized and presented in the lower graph.

FIGS. 2A and 2B. Scatter plot-comparing phosphorylation of Erk1/2 between AD and AC cells after 10 min of BK stimulation (FIG. 2A). Cells from 20 AD patients and 22 age-matched controls were treated with BK and processed as described in the description of FIG. 1. Activated and the total Erk1/2 were detected by Western blotting with appropriate antibodies. Results were processed and analyzed as described for FIG. 1. FIG. 2B shows BK-stimulated Erk1/2 phosphorylation from three independent replications for each randomly selected cell line.

FIGS. 3A1, 3A2, 3B1 and 3B2. Immunocytochemical staining of activated Erk1/2 in the human fibroblasts. Fibroblasts from AD patients and the age-matched controls were cultured on glass cover slips and stimulated with 10 nM BK for 10 min. Activated Erk1/2 was detected with an anti-phospho-Erk1/Erk2 antibody. The results showed that there were no apparent difference in AC cells (top image) between pre- and after BK treatment. In the AD cells, however, highly enhanced immunofluorescent signals (lower right image, 3B2) were seen in the BK-treated cells (10 min).

FIGS. 4A1, 4A2, 4B1, 4B2, 4C1, 4C2, 4D1 and 4D2. Effects of different inhibitors on BK-stimulated activation of Erk1/2: Fibroblasts from AD patients and the age-matched controls were respectively preincubated at 37° C. with 50 μM 2APB for 30 min (FIG. 4A); 5 μM BiSm-1 for 15 min (FIG. 4B); 10 μM PP1 for 15 min (FIG. 4C) and 5 μM LY294002 for 15 min (FIG. 4D). A second flask of cells of each cell line was incubated with an identical volume of DMSO vehicle. At the end of incubation, cells were treated with 10 nM BK for 5 min before the reaction was terminated. The activated and "regular" forms of Erk1/2 were then detected in Western blots with the two antibodies described above. The panels at left show representative Western blots and the graphs at right summarize results from 11 cell lines from both AD and AC. ** $p<0.001$; * $p<0.05$.

FIGS. 5A, 5B1, 5B2, 5C1 and 5C2. Changes in phosphorylation of, and amounts of CREB after BK stimulation. AC and AD cells were treated with 10 nM BK for 5 or 10 min. Phosphorylated CREB (P-CREB) was measured using a anti-phospho-CREB-Ser133 antibody on Western blots. The mean densities of P-CREB were normalized against the total amount of CREB measured using an anti-"regular CREB" antibody and subjected to statistic analyses. FIG. 5A shows the BK-induced CREB phosphorylation at 5 and 10 min post-treatment. FIG. 5B shows a representative blot of P-CREB at 10 min after BK treatment. FIG. 5C shows that the total amount of CREB was significantly reduced after 10 min BK treatment.

FIGS. 6A1, 6A2, 6B1, 6B2, 6C1 and 6C2. Effects of different inhibitors on BK-stimulated phosphorylation of CREB. AC and AD cells were preincubated at 37° C. for 15 min with 5 μM BiSM-1 (FIG. 6A), 10 μM PP1 (FIG. 6B), or 5 μM Ly294002 (FIG. 6C) before incubation with 10 nM BK for 10 min. Normalization was performed as with FIGS. 5A-5C and statistical significance of differences were evaluated by 2-way ANOVA. ** $p<0.0001$; * $p<0.05$.

FIGS. 7A and 7B. Distribution of BKb2 receptor in the human skin fibroblasts. Fibroblasts were incubated with an anti-BKb2 receptor antibody followed by a fluorescein-labeled secondary antibody. The top panel shows the differential interference contrast (DIC) image of the cells, and the lower panel shows the immunofluorescence of the BK b2 receptor in fibroblasts.

DETAILED DESCRIPTION OF THE INVENTION

Figure 1:
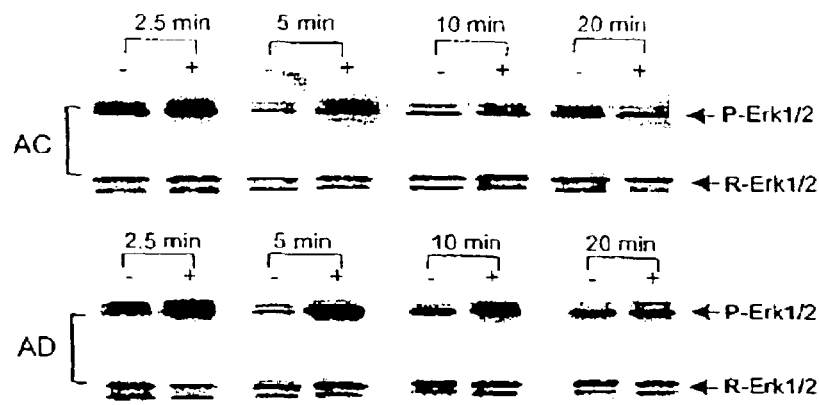
Figure 1:
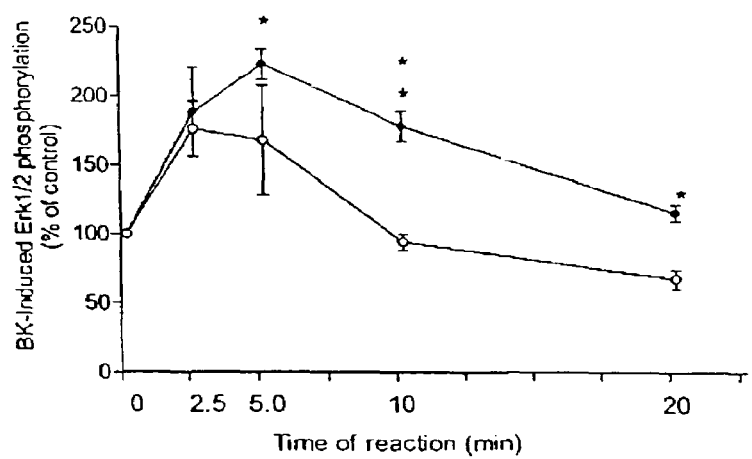

According to the invention, an activator, or agent that stimulates an IP3 mediated intracellular calcium release is one which can be identified by a person of ordinary skill in the art using the methods disclosed herein, based on published information about the IP3 receptor and related pathways, as described in the background.

An abnormally elevated level or ratio of stimulated/unstimulated phosphorylation levels means one which exceeds a previously determined level for known non-Alzheimer's disease cells at a predetermined time, by an amount that is statistically significantly characteristic of Alzheimer's disease cells and not characteristic of non-Alzheimer's disease cells.

The term indicator protein, or MAPK protein, generally used interchangeably herein, means a protein which is phosphorylated as part of the calcium signaling pathway, in response to administration of an activator compound, and whose degree of phosphorylation is differentially higher in AD cells than control cells. The indicator protein may be a calcium signaling pathway protein whose phosphorylation is associated with IP3R-sensitive $Ca^{2+}$ elevation in the cells. Indicator/MAPK proteins include those which are phosphorylated in response to IP3R mediated calcium release, such as Erk1/2.

The activation or stimulation of cells means that the intact cells are contacted with the activator in vitro, typically by adding a solution containing the activator compound, or otherwise as would be known to a person of ordinary skill in the art.

An activator compound is one that, upon introduction to human cells, stimulates phosphorylation of the indicator protein. Activator compounds elicit a differential response in the phosphorylation level of the indicator protein in cells of Alzheimer's subjects as compared to the level in control cells of a non-Alzheimer's subject. Activator compounds are effective when delivered in cell culture medium. Activator compounds may be referred to as IP3R agonists because they induce an IP3R mediated intracellular $Ca^{2+}$ elevation, either directly or indirectly.

The phosphorylation level of an indicator protein is generally determined by measuring the amount of phosphorylated indicator protein and, optionally, of unphosphorylated indicator protein, and normalizing the amount of phosphorylated protein to the total of indicator protein in the sample being analyzed. The calculated response phosphorylation level and the basal or background phosphorylation levels are thus not affected by differences in the absolute quantity of the indicator protein at a given time.

The discriminatory time point, or predetermined time after stimulating the cells with the activator compound is selected to achieve a calibrated statistically significant difference between the phosphorylation level of indicator protein in known AD cells and known control cells. The difference may be maximal at the predetermined time but that is not required and depends on other parameters of the test.

For any given activator compound, there are a finite number of suitable indicator proteins and vice versa. According to the invention, the activator compound and indicator protein combination is selected such that the activator elicits a differential response in the phosphorylation level of the indicator protein in cells of Alzheimer's subjects as compared to the level in a healthy control cells at a predetermined time after contacting the cells with the activator. A person of ordinary skill may select suitable indicator proteins and activator compounds by determining whether such a differential phosphorylation occurs. Having selected a set of indicator proteins and activator compounds, the assay parameters may then be optimized as to the discriminatory time point, suitable concentrations of the protein and activator, suitable antibodies to the phosphoproteins or unphosphorylated proteins, or other detection means, and so on.

Calculation of a ratio of the activated phosphorylation level to the basal phosphorylation level may of course be reversed. That is, for convenience we refer to the activated:basal ratio being higher than a known level, it is apparent to those skilled in the art that reversing the numerator and denominator in the ratio gives the same result if the viewed from the perspective of the unactivated phosphorylation is considered lower than a known level. Thus, where calculation of the ratio is described one way herein it is to be understood to encompass calculating the inverse as is apparent to a person of ordinary skill. Also, whereas the calculation of ratios as described herein is beneficial in providing useful comparative numbers, calculation of absolute differences between activated and basal phosphorylation levels, and between test subjects and control subjects, could also be employed and would be effective according to the invention The previously determined ratios for known Alzheimer's disease cells and non-Alzheimer's disease cells at the predetermined or discriminatory time may be written in a chart or set forth in a computer database from which diagnostic results may be determined. Accordingly, in practice, a diagnostic test is performed, an activated/basal phosphorylation ratio is calculated, and if the calculated ratio is the same as or greater than the previously determined ratio for known Alzheimer's disease cells, the diagnosis is positive. If the calculated ratio is less than the previously determined ratio for known non-Alzheimer's disease cells, the diagnosis is negative.

The present invention provides a diagnostic test for AD that comprises measurement of the response of a MAP kinase (MAPK) protein to BK stimulation. The response in AD cells is compared to the response in cells from age-matched controls (which may include subjects with other diseases, including other diseases associated with dementia). In a preferred embodiment, the test is based on the detection of abnormally high phosphorylation of Erk1/Erk2 in skin fibroblasts as diagnostic of the presence of AD (of both familial and non-familial type) after stimulation of the cells with BK. Evaluation of phosphorylation may be by Western blotting or other approaches.

Phosphorylation is a biochemical reaction in which a phosphate group is added to Ser, Thr or Tyr residues of a protein and is catalyzed by protein kinase enzymes. Phosphorylation normally modifies the functions of target proteins, typically causing activation. As part of the cell's homeostatic mechanisms, phosphorylation is only a transient process which is reversed by other enzyme called phosphatases. Any aberration in either side of the reaction (phosphorylation vs. dephosphorylation) can disrupt cellular function. These disruptions may be the fundamental underpinnings of various brain diseases.

According to the invention abnormal phosphorylation activity producing elevated phosphorylation of indicator proteins in response to calcium signaling pathway modulators can be detected in AD patients in a diagnostic analysis. The abnormality is an increase or decrease of phosphorylation at a given time relative to the levels in a healthy patient's cells. Detection of AD-specific differences in MAPK in any peripheral tissue (i.e., outside the central nervous system) serves as the basis for an economical test for early diagnosis of AD and for screening and identification of therapeutic targets for drug development. Thus, this invention provides methods, reagents, and kits for detecting the presence or absence of AD.

MAPK enzymes play a central role in conveying extracellular signals to the cell nucleus leading to control of gene expression. They are also involved in regulating phosphorylation of the microtubule-associated protein tau and generation and secretion of the β amyloid protein, events critical to the pathogenesis of AD. According to the invention, abnormally prolonged phosphorylation of the MAPK Erk1/2 occurs in, and is detected in, AD fibroblasts in response to stimulation by BK when compared to age-matched controls.

Although the present inventors conducted their initial tests with BK as the stimulus, it is to be understood that BK represents but one way to achieve stimulation of cellular IP3 receptors. Accordingly, reference herein to BK should be interpreted to encompass other suitable activator or stimulus compounds. This stimulation serves as the common step that results in the heightened Erk1/2 phosphorylation characteristic of AD. Indeed, it was observed that inhibition of the IP3 receptor totally abolished the BK-stimulated Erk1/2 phosphorylation suggesting that the IP3-sensitive $Ca^{2+}$ release accounts for this outcome. The AD-specific increases in Erk1/2 phosphorylation were also associated with enhanced expression of genes for PKC and MAP kinase kinase (also known as "MAPK/Erk kinase or MEK) isoforms in AD cells, as well as reduced expression in genes for phosphatase 1, 2A, and 2B which dephosphorylate the microtubule-associated protein tau and MAPK. The alterations of gene expression in AD cells may change the balance of activities between protein kinases and phosphatases that could contribute to this AD-specific prolonged Erk1/2 activation, as well as to the hyperphosphorylation of tau that forms neurofibrillary tangles in the AD brain. Detection of these Erk1/2 abnormal activities in skin fibroblasts reflects similar changes in the brain, and thus is diagnostic of the early pathophysiology of AD.

Thus, according to the invention, BK stimulation evokes an abnormally prolonged increase in phosphorylation of Erk1/2 in AD fibroblasts, a change that depends upon IP3 receptor-mediated $Ca^{2+}$ release. While the IP3 kinase appears to be involved in the BK-stimulated Erk1/2 phosphorylation in cells from non-AD controls, this phosphorylation of Erk1/2 in the AD cells is IP3 kinase-independent.

The AD-specific increase in Erk1/2 phosphorylation was subsequent to the IP3-mediated $Ca^{2+}$ release. Protein Kinase C (PKC) and the nonreceptor protein tyrosine kinase (PTK) c-Src are involved in the upstream signaling pathway of the Erk1/2 activation, indicating by the results that both the PKC inhibitor bisindolylmaleimide-1 and the c-Src inhibitor, PP1, completely abolished the BK-stimulated Erk1/2 phosphorylation. The PI-3 kinase, LY924002, partially inhibited the BK-stimulated Erk1/2 phosphorylation in the control, nonAD cells, but showed no effect in the AD cells, suggesting the BK-induced Erk1/2 phosphorylation may involve signaling pathways independent of PI-3 kinase.

Activation of cAMP-responsive element binding protein (CREB), measured as an increase in phosphorylation at Ser-133 was also observed after BK stimulation. Similar to Erk1/2 phosphorylation, the BK-induced CREB phosphorylation was completely inhibited by inhibitors of PKC and c-src in both AC and AD cells. Only the CREB phosphorylation in the AC but not the AD cells was partially inhibited by IP-3 kinase inhibitor LY-294002.

These results suggest a derangement of signaling pathways in response to BK in AD cells leading to abnormally enhanced and prolonged Erk1/2 phosphorylation and activation which, in turn perturb cellular processes such as gene transcription, APP (amyloid precursor protein) processing and tau protein phosphorylation, all of which underlie the pathogenesis of AD. The understanding of alterations in these pathways may also help explain the early memory loss that is a hallmark of AD. Moreover, detection of AD-specific differences in MAPK in peripheral tissues provides (1) an efficient means for early diagnosis of AD and (2) a biochemical basis for identifying therapeutic targets for drug development.

In view of the foregoing, and because the same cell may use different combinations of intracellular $Ca^{2+}$-releasing messengers to encode different external messages, any agent that is capable of stimulating IP3 receptors to cause release of internal stores of calcium, may be used in the test of the present invention an inducer of the increased Erk1/2 phosphorylation characteristic of AD cells. Again, BK is but one such agent, and other BK receptor agonists are similarly useful. Molecules that are ligands for the IP3 receptor may also be used. Because the IP3 receptor is regulated by ATP, calcium, and phosphorylation by protein kinase A, protein kinase C, and $Ca^{2+}$ caltiodulin-dependent protein kinase 11 (CaM kinase II), agents that modulate the levels or activities of ATP or these kinases can achieve similar effects and can substitute for BK in the present invention.

One such agent is the 14 amino acid peptide bombesin (Anastasi A. et al., *Arch Biochem Biophys,* 1972, 148:443-446); Woodruff G N et al., *Ann N Y Acad Sci,* 1996, 780:223-243, or biologically active analogues or fragments thereof (Rivier J E et al., *Biochemistry,* 1978, 17:1766-71; Orloff M S et al., *Peptides,* 1984 5:865-70; Walsh, J H et al., *Peptides,* 1985, 6 Suppl 3:63-68). Another is cholecysokinin. For bombesin and cholecytokinin induced calcium, signaling via IP3 and IP3 receptors, see, e.g., Cook S J et al., *Biochem J,* 1990, 265:617-620 Schulz I et al., *Biol Chem,* 1999, 380:903-908; Burdakov D, et al., *Curr Biol,* 2000, 10:993-996 Although the test is exemplified herein using skin fibroblasts, other cells that are as or more convenient to obtain and process may be used in the test of this invention, thus blood cells, preferably lymphocytes or monocytes, are easily prepared from peripheral blood and used in accordance with this invention. A person of ordinary skill can calibrate the suitable time points and experimental conditions to obtain a diagnostic method based on such cells, using suitable indicator proteins and activator compounds.

The present inventors discovered that the activity of an important enzyme, MAPK, meaning mitogen-activated protein kinase (MAP kinase) was stimulated for an abnormally prolonged interval in Alzheimer's disease skin fibroblasts compared to cells from age-matched controls. The Examples below show that phosphorylation of Erk1/2 was prolonged in AD fibroblasts upon stimulation with BK. IP3 receptor-mediated $Ca^{2+}$ release, and the activity of PKC and of the non-receptor protein tyrosine kinase (PTK) c-Src are essential for this Erk1/2 phosphorylation. Although an IP3 kinase appears to be involved in BK-stimulated Erk1/2 phosphorylation in AC cells, the same phosphorylation in AD cells is IP3 kinase-independent.

According to the invention, cells are stimulated with an agent that stimulates the IP3 receptor to release intracellular calcium; examples of such agents are BK and its analogs. BK is a potent nonapeptide that binds to and activates specific BK receptor(s), which, in turn triggers a cascade of molecular events inside the cell including stimulation of IP3 receptor and the phosphorylation of MAPK proteins. Phosphorylation is a biochemical reaction in which a phosphate group is attached to a protein initiated by an enzyme called protein kinase; it normally modifies functions of target proteins and usually causes activation of a protein. Cells need to maintain a balanced system for their functions so phosphorylation is only a transient process, which needs to be reversed by another enzyme, called phosphatase. Any aberration in either side of the reaction (phosphorylation vs. dephosphorylation) will break the integrity molecular network and disrupt cellular functions. These disruptions may be the fundamental underpinnings of various brain diseases.

Such long-lasting phosphorylation of MAPK in AD fibroblasts indicates abnormally enhanced activity of this enzyme in those cells. This AD-specific effect appears to be related to other abnormal cellular and enzymatic activities. The prolonged MAPK phosphorylation was secondary to excessive $Ca^{2+}$ release mediated by IP3 receptors from a specific store inside the cell.

Phosphorylation of MAPK was partially dependent on PI3 kinase activity, and a PI3 kinase-dependent mechanism was shown to be involved in phosphorylation of MAPK in AD cells.

In comparing the gene expression profile in AD cells with the age-matched control cells, the present inventors found that expression of PKC and MEK was increased in AD cells. Both PKC and MEK are upstream molecules that catalyze phosphorylation of MAPK. The present inventors also found reduced expression of several phosphatases that dephosphorylate MAPK. Therefore, the imbalance, ie, combined changes in the amounts and activities of enzymes that regulate MAPK phosphorylation account for the diagnostically-useful difference in AD cells—prolonged MAPK phosphorylation.

This is the first discovery of abnormally enhanced MAPK activity in AD. The MAPK family of enzymes performs crucial steps in cell signaling from the cell membrane to the nucleus. They are stimulated by a variety of signals (e.g., mitogens) acting at the cell surface and leading to cell division (mitosis), a process required for growth and development, as well as replacement and/or repair of cells damaged by injury or disease.

MAPK also plays an important role in transmitting signals in neurons that underlie functions such as learning and memory formation. MAPK also regulates secretion of the amyloid peptide βAP and phosphorylation of tau protein in brain cells. Accumulation of βAP outside nerve cells and excessive phosphorylation of tau are highly toxic to neurons, leading to plaques and neurofibrillary tangles (NFT), respectively. Indeed these are two characteristic pathological features in AD brains.

According to the present invention, abnormally enhanced MAPK activity contributes to aberrant amyloid processing and tau protein function. The present results provide new insights into molecular substrates for normal memory formation in the brain as well as pathophysiology of AD. This latter understanding is expected to lead to the identification of new molecular targets for prevention and treatment of the disease.

More practically for now, the present results have immediate clinical diagnostic significance. Because (a) skin fibroblasts manifest the alternations in MAPK activity characteristic of AD, both familial and non-familial, (b) skin fibroblasts are so easily obtained (vs. brain tissue), a, a diagnostic test based on MAPK performed on skin fibroblasts provides an simple and economic test for early diagnosis of AD.

The present new discoveries are consistent with finding by others that excessive calcium signaling was detectable in BK-stimulated AD fibroblasts (Ito et al., 1994; Gibson et at., 1996; Etcheberrigaray, et al., 1998).

EXAMPLE I

The present study used skin fibroblasts from 20 AD patients with ages ranging from 52-67 years and from 22 age-matched controls. Some of the samples were previously banked cells, while others were freshly collected and cultured from human skin.

Materials and Methods

Banked skin fibroblasts from familial (FAD) and nonfamilial (nFAD) AD patients and from the age-matched controls (AC) were purchased from the Coriell Institute for Medical Research. The medium was Dulbecco's modified Eagle's medium (DMEM; Gibco BRL) supplemented with fetal bovine serum (FBS; Bio Fluids). Bradykinin, diphenylboric acid 2-aminoethyl ester (2ABP), protease and phosphatase inhibitor cocktails were from Sigma; bisindolylmaleimide-1 (BiSM-1) and LY294002 were from Alexis; PP1 was from Dr Anthony Bishop, Princeton University. Anti Phospho-Erk1/2, anti-phospho-CREB, and anti-CREB antibodies were from Cell Signaling Technology. Anti-Erk1/2 antibody was from Upstate Biotechnology. 4-20% SDS-mini gels were from Invertrogene Novex. Nitrocellulose membranes were from Schleicher & Schuell. All the SDS electrophoresis reagents were from BioRad. SuperSignal chemiluminescent substrate kit was from Pierce.

Culture of AC and AD fibroblasts: Banked fibroblasts from Alzheimer's disease patients including both familial (FAD) nonfamilial (nFAD) types, and from the age-matched controls (AC) were maintained and passaged in T-25/T75 flasks with the DMEM+10% FBS. Cells were from subjects ranging in age from 52 to 67 years and over 80% of the samples were from males. The cells were used during passages 6-17.

Processing and culture of fibroblasts from fresh biopsies: The collection and culture of fibroblasts from freshly obtained skin tissue were performed as follows. Punch biopsy skin tissues from NFAD patients and the age-matched controls were taken by qualified personnel at Copper Ridge Institute (Sykesville, Md.) and Johns Hopkins Hospital (Baltimore, Md.) under an approved protocol. Samples were placed in 1×PBS and transported in transfer medium to the laboratory for processing. Tissue was removed from transfer medium, rinsed with PBS and chopped into 1 mm explants. The explants were transferred individually onto the growth surface of vented T-25 flasks with 3 ml of biopsy medium containing 45% FBS and 100 U/ml Penicillin and 100 U/ml streptomycin (Pen/Strep). The tissues were cultured at 37° C. for 24 hours before addition of 2 ml of biopsy medium containing 10% FBS. The medium was replaced, after 48 hours, with 5 ml of regular culture medium containing 10% FBS and Pen/Strep. The cells were then passaged and maintained as above.

Treatment of fibroblast cells with different pharmacological agents: Fibroblasts were treated with BK, and various inhibitors. These include the IP3 receptor inhibitor, diphenylboric acid 2-aminoethyl ester (2ABP, the protein kinase C inhibitor Bisindolylmaleimide I (BiSM-1), C-src protein tyrosine kinase inhibitor PP1, and PI3 kinase inhibitor LY294002.

Banked AC and AD fibroblasts were grown to 80-100% confluence before they were "starved" in a serum-free DMEM overnight. Cells were treated with 10 nM BK at 37° C. for different intervals to establish a time course for BK effects. The same volume of PBS was added to a control flask of cells of each line. The reaction was terminated by removing the medium, rapidly rinsing the cells with pre-cooled PBS, pH 7.4, and transferring the flask onto dry ice/ethanol.

Cells from fresh biopsy tissue were incubated with an optimal concentration of BK, 0.1 nM for 10 min at 37° C.

For inhibition studies, cells were preincubated with the following concentration of inhibitor at 37° C. for the intervals indicated: 2ABP (50 µM for 30 min); PP1 (10 µM for 15 min); Ly294002 (5 µM for 15 min); and BiSM-1 (5 µM for 15 min). A parallel control flask was incubated with an identical volume of DMSO vehicle. At the end of this incubation, the same inhibitor at the indicated concentration was added and followed immediately by BK to a final concentration of 10 nM. BK (10 nM) was also added to DMSO controls. Basal controls were cells to which neither BK nor inhibitors were added. After a 5-min incubation at 37° C., the reaction was terminated as above.

Cell lysates were prepared from cells of the various groups. Flasks were moved from dry ice/ethanol to ice water. Each flask received 1 ml of lysis buffer (10 mM Tris pH 7.4, 150 mM NaCl, 1 mM EDTA, 1 mM EGTA, pH8, 0.5% NP-40, 1% Triton X-100, 1% protease inhibitor cocktail (Sigma), 1% cocktail of serine/threonine (Ser/Thr) phosphatase inhibitor and tyrosine (Tyr) phosphatase inhibitor (Sigma). After rocking on an end-to-end shaker in a cold room for 30 min, cells were collected from each flask with a cell scraper. Cells were sonicated, centrifuged at 5000 rpm for 5 min, and a sample of the supernatant was subjected to Western blotting.

Western blotting: Cell lysates were boiled in an equal volume of 2×SDS-sample buffer for 10 min. Proteins from each sample were resolved on a 4-20% mini gradient gel and transferred onto a nitrocellulose membrane. Phosphorylated Erk1/2 was detected with anti-phospho-Erk1/2 antibody using the SuperSignal ECL detection kit. In order to normalize the amount of phosphorylated Erk1/2 against the total amount of Erk1/2, the same membrane blotted with the antibody was stripped with a stripping buffer (62.5 mM Tris-HCl pH6.7, 2% SDS and 100 mM 2-mercaptoethanol) at 60° C. for 45 min. After washing with 10 mM PBS pH 7.4 containing 0.01% Tween-20 (3×at 10 min), the membrane was blotted with an anti-non-phospho-Erk1/2 antibody, which allowed calculation of the total amount of Erk1/2 loaded on the gel.

CREB was detected using analogous methods.

Data analysis: Signals from phosphorylated and nonphosphorylated Erk1/2 (or CREB) were scanned with a Fujifilm LAS-1000 Plus scanner. The mean optical density of each protein band was measured using NIH Image software. Values from the phosph-Erk1/2 signals were normalized respectively against the total signal of Erk1/2. After normalization, data from treated cells was converted to a percentage of the basal control and subjected to statistical analyses.

Immunocytochemistry: Fibroblasts were grown on the surface of glass coverslips coated with 0.02 mg % polylysine. After treatment with BK as above, cells were rapidly rinsed with cold PBS, fixed with 4% formaldehyde in PBS at room temperature for 15 min, washed with PBS 3 times 5 min each, and penetrated with 0.1% TritonX-100 in PBS at room temperature for 30 min. After incubated with 10% normal horse serum in PBS at room temperature for 30 min, cells were incubated with anti-Phospho-Erk1/2 antibody (1:200) at 4° C. overnight. Coverslips were washed with PBS 3 times, and fluorescein-labeled anti-mouse IgG, 1:200 (Vector Lab) was added and allowed to incubate at room temperature for 60 min. Following three washes with PBS, and sealing with Vectashield (Vector Lab), immunostaining signals in the cells were observed in a florescence microscope. The intensity of the fluorsecent signals was measured with BioRad Quantity One® software (BioRad). For localization of BK receptors in the fibroblasts, a monoclonal anti BK B2 antibody was applied to the normal fibroblasts, followed by incubation with CY5-conjugated anti-mouse IgG and the cells examined by fluorescence microscopy.

Results

BK-Induced Activation of Erk1/2 in AC and AD Cells

BK elicited marked, but transient phosphorylation of Erk1/2 in human skin fibroblasts from control subjects (FIG. 1). Peak phosphorylation occurred at about 2.5 min following stimulation, after which phosphorylation of Erk1/2 declined, and returned to control levels by 10 min after stimulation. At 20 min post-BK treatment, phosphorylation of Erk1/2 was 68% of the control (FIG. 1). In cells from subjects with AD, however, increased phosphorylation levels of Erk1/2 were maintained for a markedly prolonged period (FIG. 1). Differences were statistically significant (Student's t test) at 5 min ($p<0.01$), with the greatest divergence occurred at 10 min ($p<0.0001$). This difference between AD and AC cells remained significant when measured at 20 min ($P=0.002$) after BK stimulation.

Figure 2:
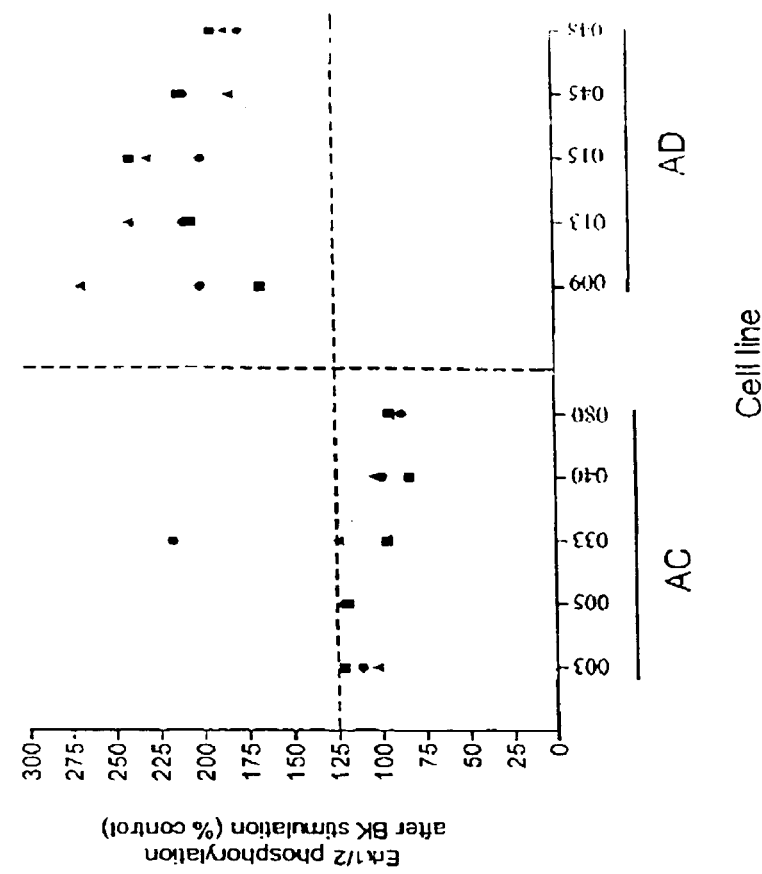
Figure 2:
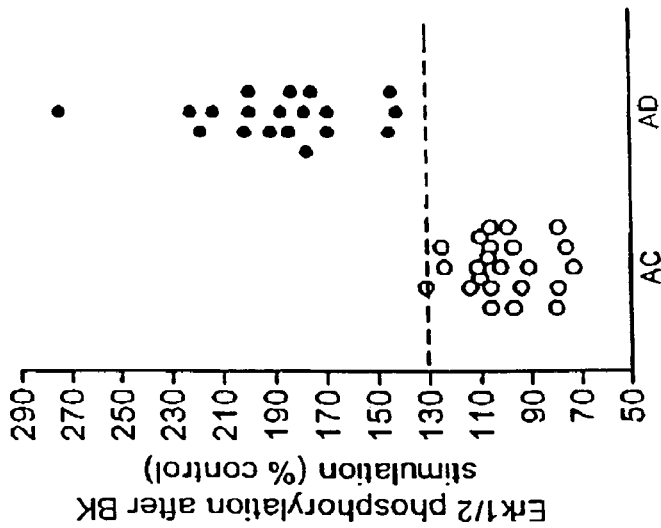

FIG. 2 shows results of a study in which BK-induced Erk1/2 phosphorylation was examined at 10 minutes after stimulation with skin fibroblasts from fresh tissue samples taken from AD patients and age-matched controls as well as from banked cells lines from AD and AC groups. Erk1/2 phosphorylation in AD fibroblasts was consistently elevated compared to age-matched controls (FIG. 2A). Similarly, BK-stimulated Erk1/2 phosphorylation in cell lines was reproducibly elevated in AD cell lines in as shown in FIG. 2B, which illustrates three independent replications (from randomly chosen AC and AD lines).

Figure 3:
Figure 3:
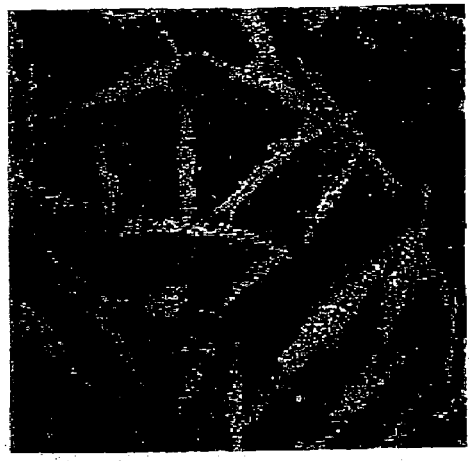
Figure 3:
Figure 3:

When fibroblasts were immunostained with anti-P-Erk1/2 antibody, increased levels of phosphorylated Erk1/2 were observed in AD cells, but not in AC cells, 10 min after -BK treatment (FIG. 3). These enhanced signals were concentrated in the para-nuclear area (FIG. 3, lower right panel).

Effects of the IP3 Receptor Inhibitor 2ABP on BK-Induced Erk1/2 Phosphorylation

Figure 4:
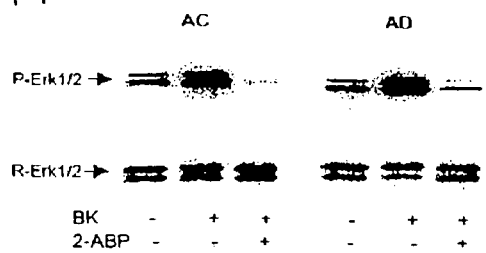
Figure 4:
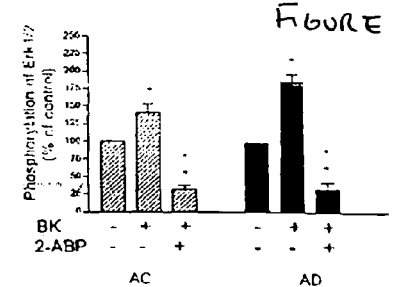
Figure 4:
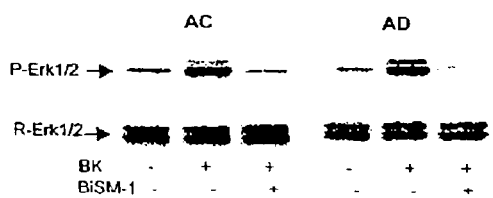
Figure 4:
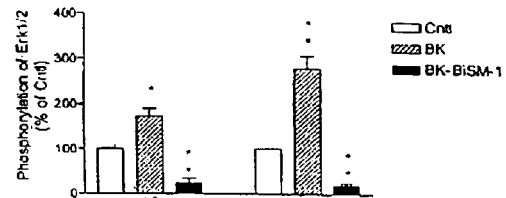
Figure 4:
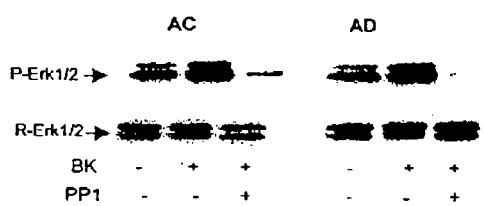
Figure 4:
Figure 4:
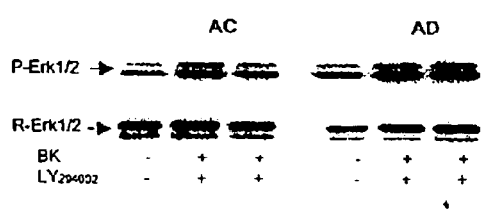
Figure 4:

BK stimulates $Ca^{2+}$ release from IP3-sensitive stores (Cruzblanca et al., 1998; Pascale et al., 1999). In the present study, the involvement of $Ca^{2+}$ release from IP3 receptor in the BK-induced Erk1/2 phosphorylation was examined. Addition of 2ABP, a potent membrane-permeable inhibitor of the IP-3R, to cells before BK completely abolished BK-stimulated Erk1/2 phosphorylation—in both AC and AD cells (FIG. 4A). Two-way ANOVA showed that the treatment effects were highly significant ($F_{1,36}=187.4$, $p<0.0001$). This result proves that phosphorylation of Erk1/2 and the subsequent molecular cascade is downstream of the IP-3R-sensitive $Ca^{2+}$ elevation in the cells.

Effect of the PKC Inhibitor BiSM-1 on the BK-Induced Erk1/2 Phosphorylation

In this experiment, AC and AD cells were preincubated with the specific PKC inhibitor BiSM-1 before BK. As shown in FIG. 4B, BK-induced phosphorylation of Erk1/2 was again abolished (in both AC and AD cells). A two-way ANOVA showed significant treatment effects. This result indicates that PKC activity is required for the BK-stimulated activation of Erk1/2 in both AC and AD cells.

Effect of the C-src Protein Tyrosine Kinase Inhibitor, PP1, on the BK-Induced Erk1/2 Phosphorylation To test whether the non receptor PTK, C-src is involved in activation of Erk1/2 by BK, AC and AD cells were preincubated with 10 µM PP1 prior to BK. Similar to 2ABP and BiSM-1, above, PP1 completely inhibited BK-induced Erk1/2 phosphorylation (FIG. 4C). Two-way ANOVA showed significant treatment effects ($F_{1,40}=234$; $p<0.0001$). This result therefore suggests that C-src PTK activity is also involved in activation of Erk1/2 by BK.

Effects of PI3 Kinase Inhibitor, LY294002, on BK-Induced Erk1/2 Phosphorylation

A study was conducted to test whether PI3 kinase activity is involved in BK-stimulated Erk1/2 activation. Fibroblasts were incubated with 5 μM LY294002 prior to BK. In contrast to the effects of inhibitors of the IP-3R, PCK and C-src, LY294002 caused a modest, though significant, inhibition of Erk1/2 phosphorylation in AC cells (FIG. 4D) while it failed to inhibit the BK-induced phosphorylation of Erk1/2 in AD cells (FIG. 4D). A two-way ANOVA showed significant treatment effects ($F_{1,20}=136.2$; $p<0.001$) and group effects ($F_{1,20}=11.55$; $p<0.05$). This result suggests that PI3 kinase activity is not involved in BK-induced Erk1/2 phosphorylation in cells of AD patients.

Effects of BK on Activation of Cyclic-AMP Response Element Binding Protein (CREB)

The effect of BK on activation of CREB, which normally is downstream of Erk1/2, was tested. As shown in FIG. 5, 10 nM BK induced highly significant phosphorylation of CREB in both AC and AD cells. The increased phosphorylation was detected as early as 5 min after BK stimulation, and increased further at 10 min (FIG. 5A). A two-way ANOVA showed a significant time effect ($F_{1,28}=14.09$, $p<0.001$) but not group effect. FIG. 5B shows similarly elevated CREB phosphorylation 10 min after BK treatment in AC and AD cells. The BK treatment also caused a marked reduction in the total amount of CREB protein at 10 min (FIG. 5C) ($p<0.001$). In summary, there were no significant differences in BK-induced CREB phosphorylation or reduction in total CREB between AC and AD cells.

Effects of PKC, C-src, and PI3 Kinase Inhibitors on BK-Induced CREB Phosphorylation Treatment of fibroblasts with the PKC inhibitor, BiSM-1, completely abolished the BK-stimulated CREB phosphorylation (FIG. 6A). A two-way ANOVA showed significant treatment effect ($F_{1,30}=53.76$, $p<0.0001$), but no group effect. Similarly, the c-src inhibitor PP1 inhibited BK-stimulated CREB phosphorylation (FIG. 6B). These results again indicate that both PKC and c-src are involved in the signaling pathway by which BK activates both Erk1/2 and CREB. Similar to the effect with Erk1/2, the PI3 kinase inhibitor, LY294002 partially inhibited CREB phosphorylation in AC but did not have any effect on CREB phosphorylation in AD cells (FIG. 6C). A two-way ANOVA showed significant treatment effect ($F_{1,30}=36.23$; $p<0.0001$) and group effect ($F_{1,30}=4.7$; $p<0.05$).

Expression of BK B2 Receptor in Fibroblasts

To test whether enhanced Erk1/2 and CREB phosphorylation in response to BK was due to an increase in the number of BK receptors expressed on AD cells, a study was performed to measure BK receptor expression in AD and control AC cells by Western blot using a specific antibody for type 2 BK receptor (BKb2R). No significant differences in receptor expression were observed.

By immunofluorescent staining, BK2bR was demonstrated in cytosol, nuclei, and paranuclear areas of fibroblasts (FIG. 7). However, no apparent differences in either intensity or distribution pattern of the BKb2R were observed in AD vs AC cells.

Discussion of Experimental Results

Fibroblasts have served as a useful model for studying AD and other hereditary diseases presumably because these cells, located all over the body, can express genetic abnormalities associated with some diseases of the brain. The present study has provided evidence that stimulation of the BK receptor results in abnormal signal transduction by the MAPK pathway in AD fibroblasts. BK is one of the most potent endogenous algesic and proinflammatory substances, playing important roles following injury, disease and CNS as well as peripheral inflammation. In the present study, BK stimulation enhanced and prolonged Erk1/2 phosphorylation in AD cells in a manner that was dependent on $Ca^{2+}$ release from IP3 receptor. This is consistent with previous reports that elevated IP3-sensitive $Ca^{2+}$ release was detected in AD skin fibroblasts following BK stimulation (Gibson et al., 1996; Etcheberrigaray et al., 1998). However, this prolonged phosphorylation of AD Erk1/2 was not due to increased expression of the BKb2 receptor or Erk1/2, since neither the expression nor concentration of these two proteins was different in AD cells compared to controls. It is not possible to rule out specific other changes in the properties or sensitivities of the BK receptor and/or IP3 receptor in AD, in addition to changes in other molecules involved in this signal transduction pathway.

The activation of the BK2bR stimulates activation of the PLC system, which in turn, together with the elevated intracellular $Ca^{2+}$, induces PKC activation. In addition, some G protein-coupled receptors ("GPCRs") are known to stimulate c-src PTK activity, which, as a key intermediate in cellular signaling, also may participate in activation of Erk1/2. The present study tested the involvement of both PKC and c-src PTK in BK-stimulated Erk1/2 phosphorylation. The fact that this phosphorylation was abolished by a PKC inhibitor, BiSM-1, and a c-src inhibitor, PP1, indicate that Erk1/2 activity is regulated by convergence of multiple upstream protein kinases. Like the IP3 receptor inhibitor, 2ABP, both BiSM-1 and PP1 abolished the Erk1/2 phosphorylation similarly in AD and control cells. It is unlikely, therefore, that the enhancement of Erk1/2 phosphorylation associated with AD was due to elevated PKC or c-src PTK activity.

In analyzing the signaling pathway(s) that underlies the AD-specific enhancement of Erk1/2 phosphorylation, the present inventors tested the involvement of PI-3 kinase, another enzyme involved in Erk1/2 activation by GPCRs. Based on studies in various systems, activation of PI-3 kinase following GPCR stimulation is dependent on activation of PKC, down stream of Ras and to involve c-src PTK. The specific PI-3 kinase inhibitor LY294002 only caused a modest inhibition of the BK-induced Erk1/2 phosphorylation in control fibroblasts but had no effect in AD cells. This suggests that, while PI-3 kinase partially contributes to the BK-activated Erk1/2 phosphorylation in normal fibroblasts, Erk1/2 phosphorylation in AD cells appears to be independent of this enzyme.

A major function of Erk1/2/MAPK is the activation of gene expression by regulation of transcriptional factors. Activation of CREB has also been observed in the present study (phosphorylation of Ser133). Unlike the phosphorylation of Erk1/2 in control cells, which lasted less than 10 min following BK treatment, highly phosphorylated CREB was present 10 min after BK treatment in both AD and control cells, suggesting a different time course for CREB activation. Inhibitors of PKC, c-src and PI3 kinase inhibit phosphorylation of CREB in a manner similar to their inhibition of Erk1/2 phosphorylation, suggesting that CREB activation is regulated by the same signal pathway. While PP1 completely inhibited BK-stimulated CREB phosphorylation, it resulted in increased expression of the CREB protein in control cells (FIG. 6B), presumably reflecting a normal compensatory feedback mechanism. This effect of PP1 was not observed in AD cells, however, suggesting that regulation of CREB expression may be impaired in AD.

Figure 6:
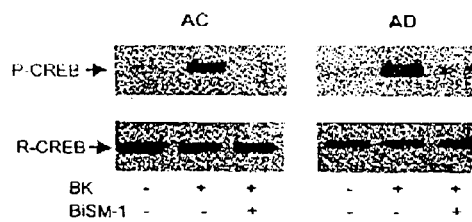
Figure 6:
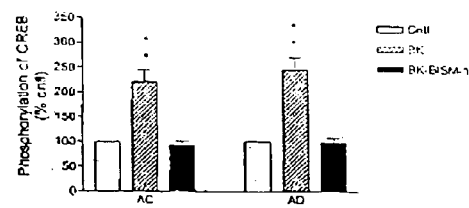
Figure 6:
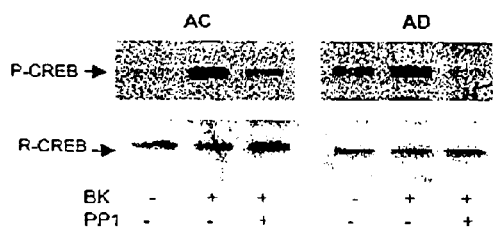
Figure 6:
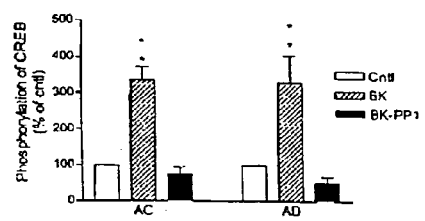
Figure 6:
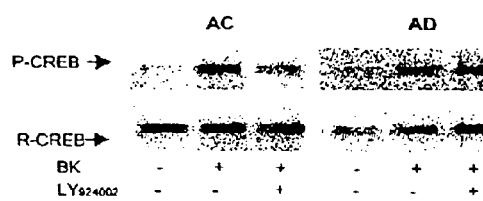
Figure 6:
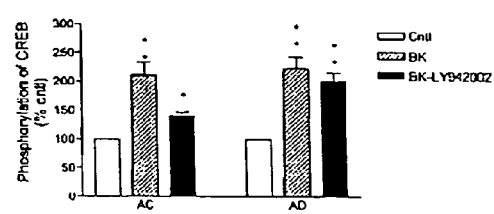

The present results provide evidence that AD pathogenesis involves derangement of molecular cascades associated with MAPK as summarized in FIG. 6. Recent results from others suggest that MAPK is important for brain functions that are related to neuronal plasticity, for example, learning and memory. Erk phosphorylates tau protein at multiple Ser/Thr sites, including Ser262 and Ser356 (Reynolds et al., 2000), which are in the microtubule-binding regions of tau. Phosphorylation of Ser262 markedly compromises the functional ability of tau to assemble and stabilize microtubules. With compromised signaling pathways involving MAPK, cells may respond to extra- and intracellular signals by inducing aberrant expression of numerous other proteins.

Systemic manifestations of abnormalities in molecular signaling such as enhanced or prolonged MAPK phosphorylation, may reflect aberrations in the CNS, e.g. memory loss, that have grave behavioral/cognitive consequences. Thus, detection of AD-specific abnormalities in MAPK and its related signaling pathways in cells found at easily accessible peripheral sites, exemplified by skin fibroblasts, provides an efficient and reliable means for early diagnosis of AD as well as for identifying therapeutic targets for drug development.

EXAMPLE 2

Figure 8:
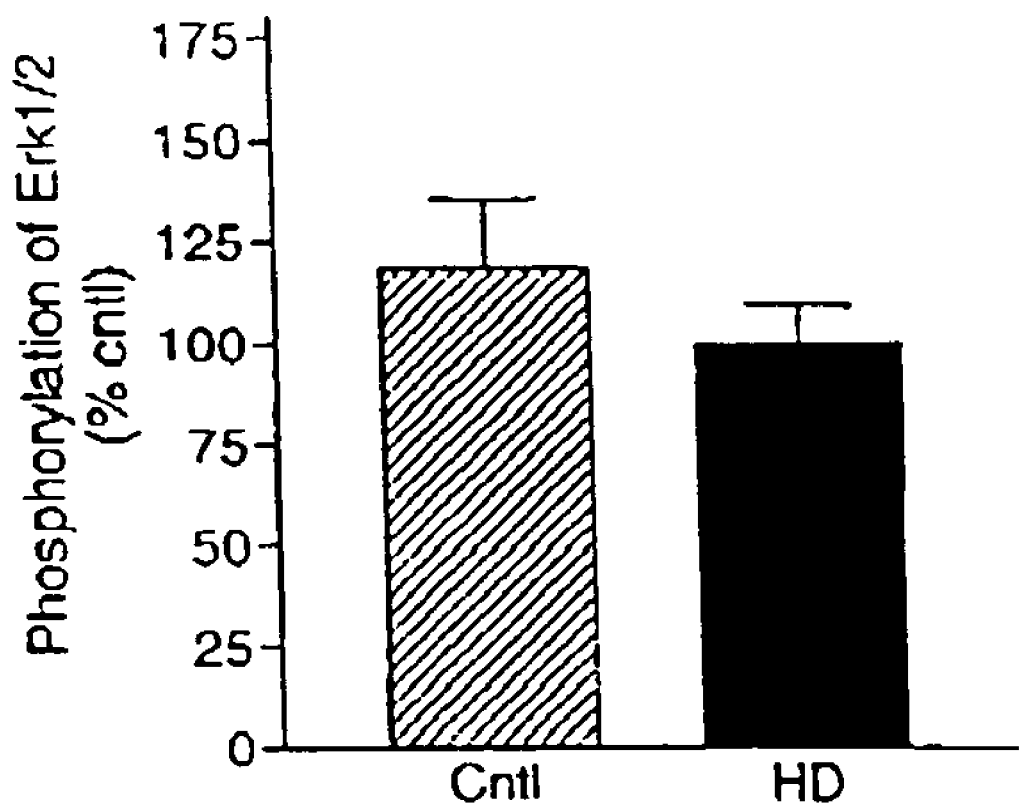
FIG. 8. The effect of bradykinin on phosphorylation of Erk1/2 on fibroblasts from individuals with Huntington's dementia (HD). N=4 and P=0.39, t test.

Using skin fibroblasts from individuals with Huntington's dementia (HD), tests were conducted to determine whether the BK-induced prolonged Erk1/2 activity was AD specific. FIG. 8 represents the effect of bradykinin on phosphorylation of Erk1/2 on fibroblasts. N=4 and P=0.39, t test. The HD cells were treated with 10 nM BK for 10 minutes. FIG. 8 shows that when HD cells were treated with 10 nM BK for 10 minutes, the phosphorylation levels of Erk1/2 were not different from that of the age-matched controls indicating that the BK-induced enhancement of Erk1/2 activity is not present in Huntington's dementia. Thus, a MAP kinase assay for Alzheimer's disease according to the invention gives a negative diagnosis for Huntington's dementia, showing that the assay is specific to Alzheimer's.

In describing preferred embodiments of the present invention, specific terminology is employed for the sake of clarity. However, the invention is not intended to be limited to the specific terminology so selected. It is to be understood that each specific element includes all technical equivalents, which operate in a similar manner to accomplish a similar purpose. The above-described embodiments of the invention may be modified or varied, and elements added or omitted, without departing from the invention, as appreciated by those skilled in the art in light of the above teachings. Each reference cited here is incorporated by reference as if each were individually incorporated by reference.

REFERENCES

U.S. provisional patent application 60/312,064, filed Feb. 27, 2001, and the following publications are incorporated herein by reference.

1. Barrow, P. A. Empson, R. M. Gladwell, S. J. Anderson, C. M. Killick, R., Yu, X., Jefferys, J. G. and Duff, K. (2000) Neurobiol Dis 7, 119-126 ("Barrow et al., 2000").
2. Bassa B V, Roh D D, Vaziri N D, Kirschenbaum M A, Kamanna V S (1999) Am J Physiol 277, F328-337 ("Bassa et al., 1999").
3. Berridge M J (1984) Biochem J 220, 345-360 ("Berridge, 1984").
4. Biemat, J., Gustke, N., Drewes, G., Mandelkow, E. W., and Mandelkow, E. (1993) Neuron 11, 153-163 ("Biernat et al., 1993").
5. Cruzblanca H, Koh D S, Hille B. (1998) Bradykinin inhibits M current via phospholipase C and $Ca^{2+}$ release from IP3-sensitive $Ca^{2+}$ stores in rat sympathetic neurons. Proc Natl Acad Sci USA 95:7151-7156 ("Cruzblanca et al., 1998").
6. Ekinci, F. J. and Shea, T. B. (1999) Cell Mol. Neurobiol. 19, 249-260 ("Ekinci and Shea, 1999").
7. Etcheberrigaray E, Gibson G E, Alkon D L (1994) Molecular mechanisms of memory and the pathophysiology of Alzheimer's disease. *Ann N Y Acad Sci* 747:245-55 ("Etcheberrigaray et al., 1994")
8. Etcheberrigaray, R., Hirashima, N., Nee, L., Prince, J., Govoni, S., Racchi, M., Tanzi, R. E. and Alkon, D. I. (1998) Neurobiol. Diseas. 5, 37-45 ("Etcheberrigaray, et al., 1998").
9. Gibson, G. E., Zhang, H., Toral-Barza, L., Szolosi, S., and Tofel-Grehl, B. (1996) Biochim, Biophys Acta 1316, 71-77 ("Gibson et al., 1996").
10. Grant S M, Morinville A, Maysinger D, Szyf M, Cuello A C. (1999) Brain Res Mol Brain Res. 72, 115-20 ("Grant et al., 1999").
11. Greenberg S M, Koo E H, Selkoe D J, Qiu W Q, Kosik K S. (1994) Secreted beta-amyloid precursor protein stimulates mitogen-activated protein kinase and enhances tau phosphorylation. *Proc Natl Acad Sci USA* 91, 7104-7108 ("Greenberg et al., 1994").
12. Hirashima, N., Etcheberrigaray, R., Bergamashi, S., Racchi, M., Battaini, F., Binetti, G., Govoni, S., Alkon, D. L. (1996) Neurobiol Aging 17, 549-555 ("Hirashima, et al., 1996"). cm 13. Ito E, Oka K, Etcheberrigaray R, Nelson T J, McPhie D L, Tofel-Grehl B, Gibson G E, Alkon D L (1994) Internal Ca2+ mobilization is altered in fibroblasts from patients with Alzheimer disease. *Proc Natl Acad Sci USA* 91,534-538 ("Ito et al., 1994").
14. Leissring, M. A., Akbari, Y., Fanger, C. M., Cahalan, M. D., Mattson, M. P. and Laferla, F. M. (2000) J Cell Biol 149, 793-798 ("Leissring et al., 2000").
15. Leissring, M. A., Parker, I., LaFerla, F. M. (1999) J Biol Chem 274, 32535-32538 ("Leissring et al., 1999").
16. Lu, Q., Soria, J. P., and Wood, J. G. (1993) J. Neurosci. Res. 35, 439-444 ("Lu et al., 1993").
17. Mattson, M. P., Zhu, H., Yu, J. and Kindy, M. S. (2000) J. Neurosci. 20, 1358-1364 ("Mattson et al., 2000").
18. McDonald D R, Bamberger M E, Combs C K, Landreth G E (1998) J Neurosci 18, 4451-4460 ("McDonald et al., 1998").
19. Pascale A, Bhagavan S, Nelson T J, Neve R L, McPhie D L, Etcheberrigaray R. (1999) Enhanced BK-induced calcium responsiveness in PC12 cells expressing the C100 fragment of the amyloid precursor protein. Brain Res Mol Brain Res 72:205-2 ("Pascale et al., 1999").
20. Putney J. W. Jr. (2000) Neuron 27, 411-412 ("Putney, 2000").
21. Reynolds, C. H., Betts, J. C., Blackstock, W. P., Nebreda, A. R. and Anderton, B. H. (2000) J. Neurochem. 74, 1587-1595 ("Reynolds et al., 2000").
22. Sheehan J P, Swerdlow R H, Miller S W, Davis R E, Parks J K, Parker W D, Tuttle J B. (1997) J Neurosci 17, 4612-4622 ("Sheehan et al., 1997").
23. Yoo, A. S., Cheng, I., Chung, S., Grenfell, T. Z., Lee, H., Pack-Chung, E., Handler, M., Shen, J., Presenilin-mediated modulation of capacitative calcium entry. Neuron. 2000 Sep;27(3):561-72 ("Yoo et al., 2000").

What is claimed is:

1. A method comprising the steps of:
   (a) measuring a basal phosphorylation level of Erk1/2 protein in cells selected from the group consisting of fibroblast, buccal mucosal, neuron, and blood from a subject;
   (b) contacting said cells from the subject with a PKC activator;
   (c) measuring an activated phosphorylation level of Erk1/2 protein in said subject cells after step (b); and
   (d) calculating a ratio of the activated phosphorylation level determined in step (c) to the basal phosphorylation level of step (a); and
   (e) comparing the calculated ratio of step (d) to a calculated ratio of activated to basal phosphorylation levels of Erk1/2 measured from known Alzheimer's disease cells, or
   comparing the calculated ratio of step (d) to a calculated ratio of activated to basal phosphorylation levels of Erk1/2 measured from non-Alzheimer's disease cells;
   wherein said method is indicative of Alzheimer's disease
      if the calculated ratio of step (d) is not higher or lower than said calculated ratio of step (e) for known Alzheimer's disease cells or
      if the calculated ratio of step (d) is higher or lower than said calculated ratio of step (e) for non-Alzheimer's disease cells.

2. A method comprising the steps of:
   (a) measuring a background phosphorylation level of Erk1/2 protein in cells selected from the group consisting of fibroblast, buccal mucosal, neuron, and blood cells from a subject;
   (b) stimulating cells of the subject by contacting said cells with an IP3R agonist;
   (c) measuring an activated phosphorylation level of the Erk1/2 protein in the contacted cells, and
   (d) comparing the activated phosphorylation level of the Erk1/2 protein in the contacted cells to the background level and the activated phosphorylation level known for a cell from an Alzheimer's disease subject or a cell from a healthy subject;
   wherein said method is indicative of Alzheimer's disease
      if the activated phosphorylation level of said contacted cells is not higher or lower than the response level for a cell from an Alzheimer's disease subject or
      if the response phosphorylation level of said contacted cells is higher or lower than the response level known for a cell from a healthy subject.

3. The method of claim 2, wherein the steps are performed in the following order: (a), (b), (c), (d).

4. The method of claim 2, comprising the steps of measuring the background phosphorylation level in a first aliquot of cells, stimulating a similar second aliquot of the cells, and measuring the activated phosphorylation level in the second aliquot.

5. The method of claim 2, wherein the measuring steps comprise an immunoassay.

6. The method of claim 2, wherein during said measuring step, said cells are disrupted cells.

7. The method of claim 2, wherein the IP3-R agonist is selected from the group consisting of bradykinin, bombesin, cholecystokinin, thrombin, prostaglandin $F_{2\alpha}$ and vasopressin.

8. A method comprising the steps of:
   (a) obtaining cells from a subject wherein said cells are selected from the group consisting of fibroblast, buccal mucosal, neuron, and blood;
   (b) measuring a basal phosphorylation level of Erk1/2 protein in said cells;
   (c) contacting said cells with a PKC activator;
   (d) measuring the phosphorylation level of Erk1/2 protein in said cells after said contacting step (c); and
   (e) calculating a first ratio of the phosphorylation level measured in step (d) to the phosphorylation level measured in step (b) and comparing said calculated first ratio to a calculated second ratio from known Alzheimer's disease cells and a calculated third ratio from known non-Alzheimer's disease cells;
   wherein said method is indicative of Alzheimer's disease
      (i) if the calculated first ratio of step (e) is not higher or lower than the second calculated ratio, or
      (ii) if the first ratio of step (e) is not higher or lower than the third calculated ratio.

9. The method of claim 1, wherein the PKC activator is selected from the group consisting of bradykinin, bombesin, cholecystokinin, thrombin, prostaglandin $F_{2\alpha}$ and vasopressin.

10. The method of claim 1, wherein the measuring steps comprise immunoassay
    wherein said cells from the subject are contacted with an antibody specific for phosphorylated Erk1/2 protein and the antibody binds to the phoshporylated Erk1/2 protein, and
    wherein said measuring step comprises detecting the antibody bound to the phosphorylated Erk1/2 protein.

11. The method of claim 10 wherein said immunoassay is a radioimmunoassay, a Western blot assay, an immunofluorescence assay, an enzyme immunoassay, an immunoprecipitation assay, a chemiluminescence assay, an immunohistochemical assay, a dot blot assay, or a slot blot assay.

12. A method comprising the steps of:
    contacting cells from a subject with a PKC activator wherein said cells are selected from the group consisting of fibroblast, buccal mucosal, neuron, and blood,
    measuring phosphorylation of Erk1/2 protein in said subject cells at one or more time points-after the contacting step, and
    comparing the measured phosphorylation of Erk1/2 protein in the subject cells to phosphorylation in non-Alzheimer's disease cells at the same time points after contacting the non-Alzheimer's disease cells with the PKC activator,
    wherein said method is indicative of a positive diagnosis of Alzheimer's disease
      if phosphorylation of Erk1/2 protein in the subject cells is increased compared to the non-Alzheimer's disease cells.

13. The method of claim 12, wherein the PKC activator is bradykinin or a bradykinin receptor agonist.

14. The method of claim 12, wherein the PKC activator is bombesin.

15. The method of claim 12, wherein the PKC activator is one which induces IP3- mediated $Ca^{2+}$ release.

16. The method of claim 12, wherein the phosphorylation is measured at a single time point after the contacting step.

17. The method of claim 12, wherein the measuring comprises measuring phosphorylation in a first aliquot of the subject cells at a first time point after the contacting step, and measuring phosphorylation in a second aliquot of the subject cells at a second time point after the contacting step.

18. The method of claim 12, wherein the time points are selected from the group consisting of one or more of about 0.5 minutes, 1 minute, 2 minutes, 2.5 minutes, 5 minutes, 10 minutes, 20 minutes, and 30 minutes.

19. The method of claim 12, wherein the cells are skin fibroblasts.

20. The method of claim 12, wherein the measuring step comprises detecting phosphorylation in a lysate of the subject cells.

21. The method of claim 12, wherein the measuring step is carried out in vitro.

22. The method of claim 12, wherein the measuring step comprises gel electrophoresis.

23. The method of claim 12, wherein the measuring step comprises Western blotting.

24. The method of claim 23, wherein the Western blotting comprises using an anti-phospho-Erk1/2 antibody.

25. The method of claim 12, wherein the increased phosphorylation is an elevated amount of phosphorylated Erk1/2 at a single time point.

26. The method of claim 12, wherein the increased phosphorylation is an increase of duration of phosphorylated Erk1/2.

27. The method of claim 12, wherein the subject lacks clinical manifestations of Alzheimer's disease.

28. The method of claim 12, further comprising preincubating the subject cells with one or more inhibitors selected from the group consisting of an inhibitor of protein kinase C activity, an inhibitor of PI-3 kinase activity, an inhibitor of C-SRC protein tyrosine kinase activity, an inhibitor of the IP-3 receptor and an inhibitor of a protein phosphatase.

29. The method of claim 12, wherein the increased phosphorylation is inhibited by preincubating the subject's cells with an inhibitor selected from the group consisting of an inhibitor of protein kinase C activity, C-src protein tyrosine kinase activity, PI-3 kinase activity, and the IP-3 receptor.

30. The method of claim 29, wherein said inhibitor is selected from the group consisting of BiSM-1, PP1, and 2-aminoethoxydiphenyl borate.

31. A method comprising the steps of:
  (a) incubating cells from a subject with a PKC activator in a diluent, wherein said cells are selected from the group consisting of fibroblast, buccal mucosal cell, neuron, and blood;
  (b) before, at the same time or after step (a) incubating cells of a same type from the subject with a control compound or with said diluent, thereby producing unstimulated control cells;
  (c) comparing a level of phosphorylated Erk1/2 protein in the cells of step (a) to a level of phosphorylated Erk1/2 protein in the unstimulated control cells;
wherein said method is indicative of a positive diagnosis of Alzheimer's disease
  if the level of the phosphorylated Erk1/2 protein in the cells of step (a) is increased as compared to the phosphorylated Erk1/2 protein in the unstimulated control cells.

32. The method of claim 31 wherein said comparing step (c) includes the following steps:
  (i) contacting a protein sample from said cells of step (a) and/or said unstimulated control cells with an antibody which recognizes the phosphorylated Erk1/2 protein; and
  (ii) detecting binding of said antibody to said phosphorylated Erk1/2 protein.

33. The method of claim 32, further comprising contacting a protein sample from said cells of step (a) and/or unstimulated control cells with an antibody which recognizes an unphosphorylated form of said Erk1/2 protein, and detecting binding of said antibody to said unphosphorylated Erk1/2 protein.

34. The method of claim 31, wherein said comparing step further comprises a step of obtaining a protein sample from said cells of step (a) and said unstimulated control cells.

35. A method comprising:
  measuring phosphorylation of Erk1/2 protein in Alzheimer's disease cells and non-Alzheimer's disease control cells and selecting a compound that increases phosphorylation of Erk1/2 protein and/or increases duration of phosphorylation of Erk1/2 protein in Alzheimer's disease cells compared to non-Alzheimer's disease control cells after contacting said cells with said compound.

36. A method comprising the steps of:
  (a) contacting skin fibroblast cells from a subject and from a non-Alzheimer's disease control subject with an effective, phosphorylation-stimulating concentration of bradykinin,
  (b) measuring the amount of phosphorylated Erk1/2 in the subject cells at one or more time points selected from the group consisting of 2 minutes, 5 minutes, 10 minutes, 20 minutes, and 30 minutes comprising Western blotting using an antibody specific for phospho-Erk1/2;
  (c) measuring phosphorylated Erk1/2 in skin fibroblast cells from a non-Alzheimer's disease control subject at the same time point or points of step (b) comprising Western blotting using an antibody specific for phospho-Erk1/2;
wherein the amount of phosphorylated Erk1/2 in steps (b) and (c) is normalized to protein in said cells;
  (d) comparing phosphorylated Erk1/2 in the subject cells with phosphorylated Erk1/2 in the non-Alzheimer's disease control cells at said time points,
wherein said method is indicative of a positive diagnosis of Alzheimer's disease
  if phosphorylated Erk1/2 in the subject cells is increased compared to the non-Alzheimer's disease control cells at one or more of said time points.

37. The method of claim 36, further comprising contacting the subject cells with one or more inhibitors selected from the group consisting of:
  (a) an inhibitor of protein kinase C activity, BiSM-1,
  (b) an inhibitor of C-src protein tyrosine kinase activity, PP1; and
  (c) an inhibitor of IP-3 receptor, 2-aminoethoxydiphenyl borate wherein the phosphorylated Erk1/2 in the subject cells of step (a) is reduced by said inhibitor compared to non-Alzheimer's disease control cells.

38. A method comprising the steps of:
  a) stimulating cells from a subject with a PKC activator that increases phosphorylation of Erk1/2 protein wherein said cells are selected from the group consisting of fibroblast, buccal mucosal, neuron, and blood, and
  b) comparing a level of unphosphorylated Erk1/2 protein and phosphorylated Erk1/2 protein in the cells of step (a) to a level of unphosphorylated Erk1/2 protein and phosphorylated Erk1/2 protein in unstimulated control cells of the same type from said subject,
wherein said method is indicative of a positive diagnosis of Alzheimer's disease
  if phosphorylated Erk1/2 protein in the cells of step (a) is increased-compared to unstimulated cells.

39. The method of claim 1, wherein said cells are disrupted during the measuring steps.

40. The method of claim 1, wherein said cells are fibroblast cells.

41. The method of claim 1, wherein said cells are buccal mucosal cells.

42. The method of claim 1, wherein said cells are neuron cells.

43. The method of claim 1, wherein said cells are blood cells.

44. The method of claim 2, wherein said cells are fibroblast cells.

45. The method of claim 2, wherein said cells are buccal mucosal cells.

46. The method of claim 2, wherein said cells are neuron cells.

47. The method of claim 2, wherein said cells are blood cells.

48. The method of claim 8, wherein said cells are fibroblast cells.

49. The method of claim 8, wherein said cells are buccal mucosal cells.

50. The method of claim 8, wherein said cells are neuron cells.

51. The method of claim 8, wherein said cells are blood cells.

52. The method of claim 12, wherein said cells are buccal mucosal cells.

53. The method of claim 12, wherein said cells are neuron cells.

54. The method of claim 12, wherein said cells are blood cells.

55. The method of claim 31, wherein said cells are fibroblast cells.

56. The method of claim 31, wherein said cells are buccal mucosal cells.

57. The method of claim 31, wherein said cells are neuron cells.

58. The method of claim 31, wherein said cells are blood cells.

59. The method of claim 38, wherein said cells are fibroblast cells.

60. The method of claim 38, wherein said cells are buccal mucosal cells.

61. The method of claim 38, wherein said cells are neuron cells.

62. The method of claim 38, wherein said cells are blood cells.

* * * * *